United States Patent [19]
Parker et al.

[11] Patent Number: 5,565,323
[45] Date of Patent: Oct. 15, 1996

[54] CYTOCHROME OXIDASE MUTATIONS AIDING DIAGNOSIS OF SPORADIC ALZHEIMER'S DISEASE

[75] Inventors: W. Davis Parker, Charlottesville, Va.; Corinna Herrnstadt, San Diego, Calif.

[73] Assignee: MitoKor, San Diego, Calif.

[21] Appl. No.: 219,842

[22] Filed: Mar. 30, 1994

[51] Int. Cl.$^6$ .............................. C12Q 1/68; C12P 19/34; C07H 21/00
[52] U.S. Cl. ........................... 435/6; 435/91.1; 435/91.2; 435/91.52; 536/23.5; 536/24.31
[58] Field of Search ......................... 435/6, 91.2, 91.52, 435/6, 91.1

[56] References Cited

PUBLICATIONS

Marzuki et al. Normal variants of human mitochondrial DNA and translation products: The building of a reference data based Hum Genet (1991) 88:139–145.

Parker et al., "Cytochrome oxidase deficiency in Alzheimer's disease." *Neurology* 40:1302–1303 (1990).

Anderson et al., "Sequence and organization of the human mitochondrial genome." *Nature* 290:457–465 (1981).

Bennett et al., "Cytochrome oxidase inhibition a novel animal model of alzheimer's disease." *J. of Geriatric Psychiatry and Neurology* 5:93–101 (1992).

Kish et al., "Brain cytochrome oxidase in alheimer's disease." *J. of Neurochemistry* 59(2):776–779 (1992).

Bowling et al., "Age–dependent impairment of mitochondrial function in primate brain." *J. of Neurochemistry* 60(5):1964–1967 (1993).

Chandrasekaran et al., "Localization of cytochrome oxidase (COX) activity and COX mRNA in the perirhinal and superior temporal sulci of the monkey brain." *Brain Research* 606:213–219 (1993).

Douglas C. Wallace, "Mitochondrial genetics: a paradigm for aging and degenerative diseases." *Science* 256:628–632 (1992).

Wallace et al., "Mitochondrial DNA mutations in epilepsy and neurological disease." *Epilepsia* 35(1):S43–S50 (1994).

Shoffner et al., "Mitochondrial DNA variants observed in alzheimer disease and parkinson disease patients." *Ognomics* 17:171–184 (1993).

Simonian et al., "Functional alterations in alzheimer's disease: diminution of cytochrome oxidase in the hippocampal formation." *J. of Neuropathy and Experimental Neurology* 52(6):580–585 (1993).

Howell et al., "Leber hereditary optic neuropathy: identification of the same mitochondrial ND1 mutation in six pedigrees." *Am. J. Hum. Genet.* 49:939–950 (1991).

Chandrasekaran et al., "Differential expression of cytochrome oxidase (COX) genes in different regions of monkey brain." *J. of Neuroscience Research* 32:415–423 (1992).

Suggs et al., "Use of synthetic oligonucleotides as hybridization probes: isolation of cloned cDNA sequences for human $\beta_2$–microglobulin." *Proc. Natl. Acad. Sci. USA* 78(11):6613–6617 (1981).

Saiki et al., "Genetic analysis of amplified DNA with immobilized sequence-specific oligonucleotide probes." *Proc. Natl. Acad. USA* 86:6230–6234 (1989).

Kuppuswamy et al., "Single nucleotide primer extension to detect genetic diseases: Experimental application to hemophilia B (factor IX) and cystic fibrosis genes." *Proc. Natl. Sci. USA* 88:1143–1147 (1991).

Syvanen et al., "A primer–guided nucleotide incorporation assay in the genotyping of apolipoprotein E." *Genomics* 8:684–692 (1990).

Landegren et al., "A ligase–mediated gene detection technique." *Science* 241:1077–1080 (1988).

Conner et al., "Detection of sickle cell $\beta^s$–globin allele by hybridization with synthetic oligonucleotides." *Proc. Natl. Acad. Sci. USA* 80:278–282 (1983).

Nickerson et al., "Automated DNA diagnostics using an ELISA–based oligonucleotide ligation assay." *Proc. Natl. Acad. Sci. USA* 87:8923–8927 (1990).

Fodor et al., "Multiplexed biochemical assays with biological chips." *Nature* 364:555–556.

Fodor et al., "Light–directed, spatially addressable parallel chemical synthesis." *Research Article* 767–773 (1991).

Matthews and Kricka, "Analytical strategies for the use of DNA probes." *Analytical Biochemistry* 169:1–25 (1988).

Francis Barany, "Genetic disease detection and DNA amplification using cloned thermostable ligase." *Proc. Natl. Acad. Sci. USA* 88:189–193 (1991).

Gibbs et al., "Detection of single DNA base differences by competitive oligonucleotide priming." *Nucleic Acids Research* 2437–2448 (1989).

Ghosh et al., "Use of maleimide–thiol coupling chemistry for efficient syntheses of oligonucleotide–enzyme conjugate hybridization probes." *Bioconjugate Chem.* 1(1)71–76 (1990).

Ishii and Ghosh, "Bead–based sandwich hybridization characteristics of oligonucleotide–alkaline phosphatase conjugates and their potential for quantitating target RNA sequences." *Bioconjugate Chem.* 4(1):34–41 (1993).

Jablonski et al., "Preparation of oligodeoxynucleotide–alkaline phosphatase conjugates and their use as hybridization probes." *Nucleic Acids Research* 14(15):6115–6129 (1986).

Li et al., "Enzyme–linked synthetic oligonucleotide probes:non–radioactive detection of enterotoxigenic *Escherichia coli* in faecal specimens." *Nucleic Acids Research* 15(13):5275–5287 (1987).

(List continued on next page.)

*Primary Examiner*—W. Gary Jones
*Assistant Examiner*—David Schreiber
*Attorney, Agent, or Firm*—Kenyon & Kenyon

[57] ABSTRACT

The present invention relates to genetic mutations in mitochondrial cytochrome oxidase genes that segregate with Alzheimer's disease (AD). The invention provides methods for detecting such mutations, as a diagnostic for Alzheimer's Disease, either before or after the onset clinical symptoms. The invention further provides treatment of cytochrome oxidase dysfunction.

16 Claims, 5 Drawing Sheets

PUBLICATIONS

Newton et al., "Analysis of any point mutation in DNA. The amplification refractory mutation system (ARMS)." *Nucleic Acids Research* 17(7):2503–2517 (1989).

Gingeras et al., "Use of self-sustained sequence replication amplification reaction to analyze and detect mutations in zidovudine-resistant human immunodeficiency virus." *J. of Infectious Diseases* 164:1066–1074 (1991).

Erlich et al., "Specific DNA amplification." *Nature* 331:461–462 (1988).

Richman et al., "Human immunodificiency virus type 1 mutants resistant to nonnucleoside inhibitors of reverse transcriptase arise in tissue culture." *Proc. Natl. Acad. Sci. USA* 88:11241–11245 (1991).

Wu and Wallace, "The ligation amplification reaction (LAR)–amplification of specific DNA sequences using sequential rounds of template–dependent ligation." *Genomics* 4:560–569 (1989).

Barany et al., *PCR Methods and App.* 1:5–16 (1991).

FIGURE 1

COX I 5'- END NON-CODING REGION AND CODING REGION: 5964-7505 (1542 bp)

AG<u>AGGCCTAA CCCCTGTCT</u>T TAGATTTTAC AGTCCAATGC TTCACTCAGC
CATTTTACCT CACCCCCACT G

ATG TTC GCC GAC CGT TGA CTA TTC TCT ACA AAC CAC AAA GAC ATT GGA ACA
CTA TAC CTA TTA TTC GGC GCA TGA GCT GGA GTC CTA GGC ACA GCT CTA AGC
CTC CTT ATT CGA GCC GAG CTG GGC CAG CCA GGC AAC CTT CTA GGT AAC GAC
CAC ATC TAC AAC GTT ATC <u>GTC ACA GCC CAT G</u>CA TTT GTA ATA ATC TTC TTC
ATA GTA ATA CCC ATC ATA ATC GGA GGC TTT GGC AAC TGA CTA GTT CCC CTA
ATA ATC GGT GCC CCC GAT ATG GCG TTT CCC CGC ATA AAC AAC ATA AGC TTC
TGA CTC TTA CCT CCC TCT CTC CTA CTC CTG CTC GCA TCT GCT ATA GTG GAG
GCC GGA GCA GGA ACA GGT TGA ACA GTC TAC CCT CCC TTA GCA GGG AAC TAC
TCC CAC <u>CCT GGA GCC TCC GTA G</u>AC CTA ACC ATC TTC TCC TTA CAC CTA GCA
GGT GTC TCC TCT ATC TTA GGG GCC ATC AAT TTC ATC ACA ACA ATT ATC AAT
ATA AAA CCC CCT GCC ATA ACC CAA TAC CAA ACG CCC CTC TTC GTC TGA TCC
GTC CTA ATC ACA GCA GTC CTA CTT CTC CTA TCT CTC CCA GTC CTA GCT GCT
GGC ATC ACT ATA CTA CTA ACA GAC CGC AAC CTC AAC ACC AC<u>C TTC TTC GAC
CCC G</u>CC GGA GGA GGA GAC CCC ATT CTA TAC CAA CAC CTA TTC TGA TTT TTC
GGT CAC CCT GAA GTT TAT ATT CTT ATC CTA CCA GGC TTC GGA ATA ATC TCC
CAT ATT GTA ACT TAC TAC TCC GGA AAA AAA GAA CCA TTT GGA TAC ATA GGT
ATG GTC TGA GCT ATG ATA TCA ATT GGA TTC CTA GGG TTT ATC GTG TGA GCA
CAC CAT ATA TTT ACA GTA GGA ATA GAC GTA GAC ACA CGA G<u>CA TAT TTC ACC
TCC G</u>CT ACC ATA ATC ATC GCT ATC CCC ACC GGC GTC AAA GTA TTT AGC TGA
CTC GCC ACA CTC CAC GGA AGC AAT ATG AAA TGA TCT GCT GCA GTG CTC TGA
GCC CTA GGA TTC ATC TTT CTT TTC ACC GTA GGT GGC CTG ACT GGC ATT GTA
TTA GCA AAC TCA TCA CTA GAC ATC GTA CTA CAC GAC ACG TAC TAC GTT GTA
GCC CAC TTC CAC TAT GT<u>C CTA TCA ATA GGA GCT</u> GTA TTT GCC ATC ATA GGA
GGC TTC ATT CAC TGA TTT CCC CTA TTC TCA GGC TAC ACC CTA GAC CAA ACC
TAC GCC AAA ATC CAT TTC ACT ATC ATA TTC ATC GGC GTA AAT CTA ACT TTC
TTC CCA CAA CAC TTT CTC GGC CTA TCC GGA ATG CCC CGA CGT TAC TCG GAC
TAC CCC GAT GCA TAC ACC ACA TGA AA<u>C ATC CTA TCA TCT GTA G</u>GC TCA TTC
ATT TCT CTA ACA GCA GTA ATA TTA ATA ATT TTC ATG ATT TGA GAA GCC TTC
GCT TCG AAG CGA AAA GTC CTA ATA GTA GAA GAA CCC TCC ATA AAC CTG GAG
TGA CTA TAT GGA TGC CCC CCA CCC TAC CAC ACA TTC GAA GAA CCC GTA TAC
ATA AAA TCT AGA

FIGURE 2

COX II 5'- END NON-CODING REGION AND CODING REGION: 7646-8329 (684 bp)

<u>AGGTATTAGA AAAACC</u>ATTT CATAACTTTG TCGTCAAAGT TAAATTATAG
GCTAAATCCT ATATATCTTA

ATG GCA CAT GCA GCG CAA GTA GGT CTA CAA GAC GCT ACT TCC CCT ATC ATA
GAA GAG CTT ATC ACC TTT CAT GAT CAC GCC CTC ATA ATC ATT TTC CTT ATC
TGC TTC CTA GTC CTG TAT GCC CTT TTC CTA ACA CTC ACA ACA AAA <u>CTA ACT
AAT ACT AAC ATC T</u>CA GAC GCT CAG GAA ATA GAA ACC GTC TGA ACT ATC CTG
CCC GCC ATC ATC CTA GTC CTC ATC GCC CTC CCA TCC CTA CGC ATC CTT TAC
ATA ACA GAC GAG GTC AAC GAT CCC TCC CTT ACC ATC AAA TCA ATT GGC CAC
CAA TGG TAC TGA ACC TAC GAG TAC ACC GAC TAC GGC GGA CTA ATC TTC AAC
TCC TAC ATA CTT CCC CCA TTA TTC CTA GAA CCA GGC GAC C<u>TG CGA CTC CTT
GAC</u> GTT GAC AAT CGA GTA GTA CTC CCG ATT GAA GCC CCC ATT CGT ATA ATA
ATT ACA TCA CAA GAC GTC TTG CAC TCA TGA GCT GTC CCC ACA TTA GGC TTA
AAA ACA GAT GCA ATT CCC GGA CGT CTA AAC CAA ACC ACT TTC ACC GCT ACA
CGA CCG GGG GTA TAC TAC GGT CAA TGC TCT GAA ATC TGT GGA GCA AAC CAC
AGT TTC ATG CCC ATC GTC CTA GAA TTA ATT CCC CTA AAA ATC TTT GAA ATA
GGG CCC GTA TTT ACC CTA TAG

FIGURE 3

COX III 5'- END NON-CODING REGION AND CODING REGION: 9267-10052 (785 bp)

TCGCTGTC<u>GC CTTAATCCAA GCC</u>TACGTTT TCACACTTCT AGTAAGCCTC
TACCTGCACG ACAACACATA

ATG ACC CAC CAA TCA CAT GCC TAT CAT ATA GTA AAA CCC AGC CCA TGA CCC
CTA ACA GGG GCC CTC TCA GCC CTC CTA ATG ACC TCC GGC CTA GCC ATG TGA
TTT CAC TTC CAC TCC ATA ACG CTC CTC ATA CTA GGC CTA CTA ACC AAC ACA
CTA ACC ATA TAC <u>CAA TGA TGG CGC GAT G</u>TA ACA CGA GAA AGC ACA TAC CAA
GGC CAC CAC ACA CCA CCT GTC CAA AAA GGC CTT CGA TAC GGG ATA ATC CTA
TTT ATT ACC TCA GAA GTT TTT TTC TTC GCA GGA TTT TTC TGA GCC TTT TAC
CAC TCC AGC CTA GCC CCT ACC CCC CAA TTA GGA GGG CAC TGG CCC CGA ACA
GGC ATC ACC CCG CTA AAT CCC CTA GAA GTC CCA CTC CTA AAC ACA T<u>CC GTA
TTA CTC GCA TCA GGA</u> GTA TCA ATC ACC TGA GCT CAC CAT AGT CTA ATA GAA
AAC AAC CGA AAC CAA ATA ATT CAA GCA CTG CTT ATT ACA ATT TTA CTG GGT
CTC TAT TTT ACC CTC CT ACAA GCC TCA GAG TAC TTC GAG TCT CCC TTC ACC
ATT T<u>CC GAC GGC ATC TAC GGC</u> TCA ACA TTT TTT GTA GCC ACA GGC TTC CAC
GGA CTT CAC GTC ATT ATT GGC TCA ACT TTC CTC ACT ATC TGC TTC ATC CGC
CAA CTA ATA TTT CAC TTT ACA TCC AAA CAT CAC TTT GGC TTC GAA GCC GCC
GCC TGA TAC TGG CAT TTT GTA GAT GTG GTT TGA CTA TTT CTG TAT GTC TCC
ATC TAT TGA TGA GGG TCT TAC

CYTOCHROME OXIDASE PROBE SEQUENCES

Sense Probes — DNA detection of antisense strand

| GENE | AA | LENGTH (WT) | %GC | WILD TYPE | MUTANT | MUTANT |
|---|---|---|---|---|---|---|
| COX1 | 131 | 21 | 52.1 | AGTCTACCCTCCCTTAGCAGG | AGTCTACCCTACCTTAGCAGGG | |
| COX1 | 155 | 23 | 52.2 | ACCTAGCAGGTGTCTCCTCTATC | ACCTAGCAGGTATCTCCTCTATCT | |
| COX1 | 167 | 27 | 22.2 | CAATTTCATCACACAATTATCAATAT | CAATTTCATCACAGCAATTATCAATAT | |
| COX1 | 178 | 21 | 47.6 | GCCATAACCAATACCAAACG | GCCATAACCCTATACCAAACG | |
| COX1 | 193 | 23 | 47.8 | AATCACAGCAGICCTACTTCTCC | AATCACAGCAGCCCTACTTCTCC | AATCACAGCAATCCTACTTCTCC |
| COX1 | 194 | 25 | 50.0 | TCACAGCAGTCCTACTTCTCCTATC | TCACAGCAGTCTACTTCTCCTATC | |
| COX1 | 415 | 26 | 26.9 | CAAAATCCATTTCACTATCATATTCA | AAAATCCATTTCGCTATCATATTCA | |
| COX2 | 20 | 25 | 37.5 | TCATAGAAGAGCTATCACCTTTCA | TCATAGAAGAGCCTATCACCTTTCA | |
| COX2 | 22 | 24 | 37.5 | AGAGCTTATCACCTTTCATGATCA | AGAGCTTATCACTCTTTCATGATCA | |
| COX2 | 68 | 18 | 61.1 | TGAACTATCTGCCCGCC | TGAACTATCTTGCCCGCC | |
| COX2 | 71 | 18 | 61.1 | TGCCCGCCAICATCCTAG | TGCCCGCCACCATCCTAG | |
| COX2 | 74 | 21 | 52.4 | ATCATCCTAGTCCTCATCGCC | ATCATCCTAATCCTCATCGCC | |
| COX2 | 95 | 21 | 47.6 | GATCCCTCCCTTACCATCAAA | GATCCCTCCTTACCATCAAAT | GATCCCTCCCTACCATCAAA |
| COX2 | 110 | 23 | 52.2 | AACCTAGCAGIACACCGACTACG | AACCTAGCAGAGCACACCGACTAC | AACCTACGAGTGCACCGACTAC |
| COX2 | 146 | 20 | 55.0 | AGTACTCCCGATTGAAGCCC | AGTACTCCCGGTTGAAGCCC | |

FIG. 4A

CYTOCHROME OXIDASE PROBE SEQUENCES

| GENE | AA | Antisense probes LENGTH (WT) | %GC | DNA and RNA detection sense sequence WILD TYPE | MUTANT | MUTANT |
|---|---|---|---|---|---|---|
| COX1 | 131 | 21 | 52.1 | CCTGCTAAGGGAGGGTAGACT | CCCTGCTAAGGIAGGGTAGACT | |
| COX1 | 155 | 23 | 52.2 | GATAGAGGAGACACCTGCTAGGT | AGATAGAGGAGATACCTGCTAGGT | |
| COX1 | 167 | 27 | 22.2 | ATATTGATAAATTGITGTGATGAAATTG | ATATTGATAAATTGCTGTGATGAAATTG | |
| COX1 | 178 | 21 | 47.6 | CGTTTGGTATGGGTTATGGC | CGTTTGGTATAGGGTTATGGC | |
| COX1 | 193 | 23 | 47.8 | GGAGAAGTAGGACTGCTGTGATT | GGAGAAGTAGGGCTGCTGTGATT | GGAGAAGTAGGATTGCTGTGATT |
| COX1 | 194 | 25 | 50.0 | GATAGGAGAAGTAGGACTGCTGTGA | GATAGGAGAAGTAGAGACTGCTGTGA | |
| COX1 | 415 | 26 | 26.9 | TGAATATGATAGIGAAATGGATTTTG | TGAATATGATAGCGAAATGGATTTT | |
| COX2 | 20 | 25 | 37.5 | TGAAAGGTGATAAGCTCTTCTATGA | TGAAAGGTGATAGGCTCTTCTATGA | |
| COX2 | 22 | 24 | 37.5 | TGATCATGAAAGGTGATAAGCTCT | TGATCATGAAAGATGATAAGCTCT | |
| COX2 | 68 | 18 | 61.1 | GGCGGGCAGGATAGTTCA | GGCGGGCAAGATAGTTCA | |
| COX2 | 71 | 18 | 61.1 | CTAGGATGATGGCGGGCA | CTAGGATGGTGGCGGGCA | |
| COX2 | 74 | 21 | 52.4 | GGCGATGAGGACTAGGATGAT | GGCGATGAGGATTAGGATGAT | |
| COX2 | 95 | 21 | 47.6 | TTTGATGGTAAGGGAGGGATC | ATTTGATGGTAAAGGAGGGATC | TTTGATGGTAGGGGAGGGATC |
| COX2 | 110 | 23 | 52.2 | CGTAGTCGGTGTGTACTCGTAGGTT | GTAGTCGGTGTGCTCGTAGGTT | GTAGTCGGTGCACTCGTAGGTT |
| COX2 | 146 | 20 | 55.0 | GGGCTTCAATCGGGAGTACT | GGGCTTCAACCGGGAGTACT | |

FIG.4B

CYTOCHROME OXIDASE MUTATIONS AIDING DIAGNOSIS OF SPORADIC ALZHEIMER'S DISEASE

BACKGROUND OF THE INVENTION

1. Field of the Invention

The present invention relates generally to the diagnosis and treatment of Alzheimer's disease. More specifically, the invention relates to detecting genetic mutations in mitochondrial cytochrome oxidase genes as a means for diagnosing Alzheimer's disease and suppressing these same mutations in the treatment of Alzheimer's disease.

2. Background Information

Alzheimer's disease (AD) is a progressive neurodegenerative disorder that is incurable and untreatable, except symptomatically. Alzheimer's disease affects over 13 million people world-wide. Persons suffering from Alzheimer's disease may have one of two forms of this disease; familial AD or sporadic AD.

Familial Alzheimer's disease accounts for only about 5% to 10% of all Alzheimer's cases and has an unusually early-onset, generally before the age of fifty. Familial AD is inherited and follows conventional patterns of mendelian inheritance. This form of AD has been linked to nuclear chromosomal abnormalities.

In contrast, the second form of Alzheimer's disease, sporadic AD, is a late-onset disease which is not inherited or caused by nuclear chromosomal abnormalities. This late-onset form of the disease is the more common type of Alzheimer's disease and is believed to account for approximately 90 to 95 % of all Alzheimer's cases. The cause of sporadic AD is not known.

It has been recognized that some degenerative diseases, such as Leber's hereditary optic neuropathy, myoclonic epilepsy lactic acidosis and stroke (MELAS), and myoclonic epilepsy ragged red fiber syndrome, are transmitted through mitochondrial DNA defects. Mitochondrial DNA defects have also been implicated in explaining the apparently "sporadic" (nonmendelian) occurrence of some degenerative neurologic disorders, such as Parkinson's and Alzheimer's disease. Since all proteins encoded by the mitochondrial genome are components of the electron transport chain, deficits in electron transport function have been reported in Parkinson's and Alzheimer's disease. Of particular interest, it has been reported that defects in cytochrome oxidase, an important terminal component of the electron transport chain located in the mitochondria of eukaryotic cells, may be involved in Alzheimer's disease.

One report suggesting a relation between AD and cytochrome oxidase is Parker et al., *Neurology* 40: 1302–1303 (1990), which finds that patients with Alzheimer's disease have reduced cytochrome oxidase activity. It has also been shown by Bennett et al., *J. Geriatric Psychiatry and Neurology* 5:93–101 (1992), that when sodium azide, a specific inhibitor of cytochrome oxidase was infused into rats, the rats suffered impaired memory and learning (a form of dementia). The rats mimicked the effect of Alzheimer's disease in humans. In addition, the sodium azide-tested rats failed to display long term potentiation, demonstrating loss of neuronal plasticity.

Despite these findings, the exact mechanism producing the electron transport dysfunctions is not known for Alzheimer's disease, nor has a genetic or structural basis for these dysfunctions been identified. Without knowing what causes these electron transport dysfunctions and in particular the genetic or structural basis, it is difficult to diagnose or treat Alzheimer's disease, especially the predominant form, sporadic AD.

To date, the diagnosis of probable Alzheimer's disease is by clinical observation and is a diagnosis of exclusion. Unfortunately, definitive diagnosis can only be accomplished by pathological examination at autopsy. While attempts have been made to diagnose Alzheimer's disease by identifying differences in certain biological markers, including protease nexin II and apolipoprotein E alleles, this approach has not been successful. Incomplete penetrance in AD patients or crossover into normal or other disease populations makes identification of biological markers an unreliable method of diagnosis. Clearly, a reliable diagnosis of Alzheimer's at its earliest stages is critical for efficient and effective intercession and treatment of this debilitating disease. There exists a definite need for an effective diagnostic of Alzheimer's disease, and especially for the more prevalent form, sporadic AD. There exists a need for a non-invasive diagnostic that is reliable at or before the earliest manifestations of AD symptoms.

Not only does the Alzheimer's field currently lack a reliable, early means of detection, there is at present no effective therapy for AD, other than certain palliative treatments. Current therapies in clinical evaluation are designed to treat the symptoms of the disease and not impact the underlying pathology of AD. These therapies include Cognex, Velnacrine, E2020, and other similar agents known in the field. However, since the primary etiologic events in AD are not yet known in the art, rational therapies have not been designed. There exists a need for effective therapies, particularly those that address the primary cause of AD.

The present invention satisfies these needs for a useful diagnostic and effective treatment of Alzheimer's disease and provides related advantages as well.

SUMMARY OF THE INVENTION

The present invention relates to the identification of genetic mutations in mitochondrial cytochrome oxidase genes which segregate with Alzheimer's disease. The invention provides methods for detecting such mutations as a diagnostic for Alzheimer's disease, either before or after the onset of clinical symptoms. More specifically, the present invention provides a method for detecting the presence or risk of Alzheimer's disease by obtaining a biological sample containing mitochondria from a subject and determining the presence of at least one mutation in the sequence of a mitochondrial cytochrome oxidase gene which correlates with the presence or risk of Alzheimer's disease. The present invention also encompasses a method of detecting the genetic mutations which cause a predisposition to Alzheimer's disease, by first, determining the sequence of mitochondrial cytochrome oxidase genes from subjects known to have Alzheimer's disease, second, comparing the sequence to that of known wildtype mitochondrial cytochrome oxidase genes, and lastly, identifying mutations in the patients or tissues collected at autopsy. The present invention also involves isolated nucleic acid sequences which are useful in the above mentioned diagnostics, namely those which correspond, or are complementary, to portions of mitochondrial cytochrome oxidase genes, and where the sequences contain gene mutations which correlate with the presence of Alzheimer's disease.

The invention also pertains to suppression of the undesired biological activity of the mutations. This affords a therapeutic treatment for Alzheimer's disease. More specifically, invention pertains to methods of inhibiting the transcription or translation of mutant cytochrome oxidase encoding genes by contacting the genes with antisense sequences which are specific for mutant sequences and which hybridize to a target mutant cytochrome oxidase gene.

BRIEF DESCRIPTION OF THE FIGURES

FIG. 1 lists the 5' end upstream non-coding region and the complete nucleic acid sequence encoding mitochondrial cytochrome oxidase subunit I (SEQ. ID. NO. 1). The underlined sequences indicate the primers used for sequencing the nucleic acid sequence.

FIG. 2 lists the 5' end non-coding region and the complete nucleic acid sequence of the mitochondrial cytochrome oxidase subunit II coding region (SEQ. ID. NO. 2). The underlined sequences indicate the primers used for sequencing the nucleic acid sequence.

FIG. 3 lists the 5' end non-coding region and the complete nucleic acid sequence of the mitochondrial cytochrome oxidase subunit III coding region (SEQ. ID. NO. 3). The underlined sequences indicate the primers used for sequencing the nucleic acid sequence.

FIGS. 4A and 4B provide representative sequences of probes for detecting mutations in COX genes and representative antisense sequences (SEQ. ID. NO. 30–SEQ. ID. NO. 95, respectively).

DETAILED DESCRIPTION OF THE INVENTION

The present invention relates to genetic mutations in mitochondrial cytochrome oxidase genes which segregate with Alzheimer's disease. The invention provides methods for detecting such mutations, as a diagnostic for Alzheimer's disease, either before or after the onset of clinical symptoms. Moreover, the invention also pertains to suppression of the undesired biological activity of the mutations and thus affords a therapeutic treatment for Alzheimer's disease. Not only does this invention provide the first effective diagnostic of Alzheimer's disease which is reliable at or before the earliest manifestations of AD symptoms, it also provides the first effective therapy for this debilitating disease.

Cytochrome oxidase (COX) is an important terminal component of the electron transport chain located in the mitochondria of eukaryotic cells. Cytochrome oxidase, also known as complex IV of the electron transport chain, is composed of at least thirteen subunits. At least ten of these subunits are encoded in nuclear genes; the remaining three subunits (I, II, and III) are encoded by mitochondrial genes. Mitochondrial DNA (mtDNA) is a small circular DNA that is approximately 17 kB long in humans. The mtDNA encodes for two ribosomal RNAs (rRNA), a complete set of transfer RNAs (tRNA), and thirteen proteins, including the three cytochrome oxidase subunits COX I, COX II, and COX III.

Most of the mtDNA present in an individual is derived from the mtDNA contained within the ovum at the time of the individual's conception. Mutations in mtDNA sequence which affect all copies of mtDNA in an individual are known as homoplasmic. Mutations which affect only some copies of mtDNA are known as heteroplasmic and will vary between different mitochondria in the same individual.

In the present invention, mtDNA from both normal individuals and known Alzheimer's patients has been isolated, cloned and sequenced. As expected, a few non-deleterious and apparently random mutations in each gene including some normal genes, were observed. However, in the AD patients, a small number of deleterious heteroplasmic mutations at common sites were noted. For the three mitochondrial COX subunits, the mutations occurred in one or more of the subunit clones for each individual. Such mutations were especially observed in the expressed regions of COX subunits I and II of the mtDNA.

According to the present invention, such mutations in COX genes segregate with, and are possibly sufficient for, Alzheimer's disease. Sporadic AD, which accounts for at least 90% of all AD patients, is segregated with deleterious heteroplasmic mutation(s) in the mtDNA-encoded COX subunits. Detection of the deleterious mutations, therefore, is both predictive and diagnostic of Alzheimer's disease.

Suppressing the effects of the deleterious mutations through antisense technology provides an effective therapy for AD. Much is known about 'antisense' therapies targeting messenger RNA (mRNA) or nuclear DNA. The diagnostic test of the present invention can be used to determine which of the specific AD mutations exist in a particular AD patient; this allows for "custom" treatment of the patient with antisense oligonucleotides only for the detected mutations. This patient-specific antisense therapy is also novel, and minimizes the exposure of the patient to any unnecessary antisense therapeutic treatment.

Throughout this application various publications are referenced within parentheses. The disclosures of these publications in their entireties are hereby incorporated by reference in this application in order to more fully describe the state of the art to which this invention pertains.

Blood and brain samples were harvested and DNA isolated from a number of clinically-classified or autopsy confirmed AD patients, and from a number of documented age-matched 'normals' (elderly individuals with no history of AD or any sign of clinical symptoms of AD) or age-matched neurodegenerative disease controls (patients with Huntington's disease, supranuclear palsy, etc.). After cloning of cytochrome oxidase (COX) gene fragments, the sequences of multiple clones from each patient were obtained. Compilation of the sequences were made, aligned, and compared with published Cambridge and Genbank sequences (Anderson et al., Nature 290:457–465 (1981)) for known normal human COX genes. The published Cambridge coding sequences are numbered as follows: COX I is nucleotides 5964 to 7505, COX II is nucleotides 7646 to 8329, and COX III is nucleotides 9267 to 10052. The corresponding sequences are numbered as follows in Anderson et al., Nature 290:457–465, (1981): COX I is nucleotides 5904 to 7445, COX II is nucleotides 7586 to 8269, and COX III is nucleotides 9207 to 9992. All reference hereinbelow is made only to the published Cambridge sequences, though it will be appreciated by those of skill in the art that the corresponding sequences, following a different numbering scheme, including Anderson's, could be used in the invention.

Any variation (mutation, insertion, or deletion) from published sequences was verified by replication and by complementary strand sequencing. Analysis of the variations in known AD patients indicated a significant number of mutations. Some of the mutations observed were 'silent' mutations resulting in no amino acid changes in the expressed protein. However, a number of mutations present would result in amino acid changes in the corresponding protein. In many instances the corresponding amino acid change would also lead to conformational changes to the COX enzyme.

In cytochrome oxidase subunit II, for example, the sequence in AD patients varied from the normal sequence in at least one base per gene. The data is summarized in Table 2. Several of the recurrent mutations observed would result in conformational alterations of the COX enzyme. Mutation of the normal ACC observed at codon 22 to ATC results in a change from the normal hydrophilic threonine (Thr) to a hydrophobic isoleucine (Ils). Changes of this type in nucleic acid structure, particularly when occurring in highly conserved areas, are known to disrupt or modify enzymatic activity.

As described more fully herein below, each of the COX genes sequenced shows significant variation from the normal sequence at a number of specific sites, or mutational "hot spots." Moreover, these hot spots generally fell within particular regions of the COX genes. In the first 1,530 bases (510 codons) of COX I, and in particular between codons 131 and 200, codons 131, 155, 167, 178, 193, 194 and 415 have a high degree of mutational similarity in the AD sequences (see Table 1). In COX II, hot spots occur especially in the region between codon 50 and codon 150 and in particular at codons 20, 22, 68, 71, 74, 95, 110 and 146 (see Table 2). In COX III, codons 82 and 247 appear to be highly variable hot spots.

Mutations observed in COX I gene of Alzheimer's patients

Table 1 below is an example of some mutations and the number of times a given mutation was observed in the ten clones of mitochondrial cytochrome oxidase subunit I (COX I) gene for each Alzheimer's patient. The mutations listed for the AD patients are relative to the published Cambridge sequences for normal human COX I. The codon number indicated is determined in a conventional manner from the open reading frame at the 5'-end of the gene.

TABLE 1

| Codon # | 131 | 155 | 167 | 178 | 193 | 194 | 415 |
|---|---|---|---|---|---|---|---|
| Normal AA | Pro | Val | Thr | Gln | Val | Leu | Thr |
| Normal DNA | CCC | GTT | ACA | CAA | GTC | CTA | ACT |
| Observed | Thr | Ile | Ala | Leu | Ala | Phe | Ala |
| Mutation AD Patient | ACC | ATC | GCA | CTA | GCC | TTA | GCT |
| # 1KE | — | 2 | — | — | — | 1 | 2 |
| # 2RI | — | 5 | — | — | — | 4 | 5 |
| # 3DA | — | — | 1 | — | — | — | — |
| # 4WO | — | — | — | — | — | 2 | 2 |
| # 5PI | — | — | 1 | — | — | — | — |
| # 5TR | — | — | — | — | 1 | — | — |
| # 6LF | — | — | — | 1 | — | — | — |
| # 7LW | 5 | — | — | — | — | — | — |
| # 8SP | — | — | — | — | 1 | — | — |
| # 9YA | — | — | — | 1 | — | — | — |
| # 10BR | — | — | — | — | 8 | — | — |

As evidenced by Table 1, mutational hot spots of COX I in AD patients are codons 131, 155, 167, 178, 193, 194 and 415.

Mutations observed in COX II gene of Alzheimer's patients

Table 2 below is an example of some mutations and the number of times a given mutation was observed in the ten clones of mitochondrial cytochrome oxidase subunit II (COX II) gene for each Alzheimer's patient. The mutations listed for the AD patients are relative to the published Cambridge sequences for normal human COX II. The codon number indicated is determined in a conventional manner from the open reading frame at the 5'-end of the gene.

TABLE 2

| Codon # | 20 | 22 | 68 | 71 | 74 | 95 | 110 | 146 |
|---|---|---|---|---|---|---|---|---|
| Normal AA | Leu | Thr | Leu | Ile | Val | Leu | Tyr | Ile |
| Normal DNA | CTT | ACC | CTG | ATC | GTC | CTT | TAC | ATT |
| Observed | Pro | Ile | Phe | Thr | Ile | Phe | Cys | Val |
| Mutation AD Patient | CCT | ATC | TTG | ACC | ATC | TTT | CAC | GTT |
| # 1KE | — | 2 | — | — | 1 | 3 | — | 2 |
| # 2RI | — | 3 | — | — | — | 2 | — | 3 |
| # 3DA | 1 | 1 | — | — | — | — | — | — |
| # 4PI | — | — | — | 1 | — | — | — | — |
| # 5TR | — | — | — | — | — | — | 1 | — |
| # 6CR | — | — | — | 1 | — | — | 1 | — |
| # 7OB | — | — | — | — | 1 | — | — | — |
| # 8AL | — | — | — | — | 10 | — | — | — |
| # 9SA | 1 | — | 10 | — | — | — | — | — |
| # 10BR | — | — | — | — | — | 1 | 1 | — |

As evidenced by Table 2, the mutational hot spots of COX II in AD patients is codons 20, 22, 68, 71, 74, 95, 110 and 146.

At each mutational hot spot, the specific variations noted in AD patients appear universally. For example, at codon 415 in COX I, the normal codon is threonine; each of nine AD mutations observed in codon 415 in COX I codes for alanine. At position 194 in COX I, the aromatic phenylalanine codon replaces the normally hydrophobic leucine. These specific mutations do not occur randomly and are not observed in normal or neurological patients which do not have Alzheimer's disease.

The invention also includes the isolated nucleotide sequences which correspond to or are complementary to portions of mitochondrial cytochrome oxidase genes which contain gene mutations that correlate with the presence of Alzheimer's disease. The isolated nucleotide sequences which contain gene mutations include COX I nucleotides 5964 to 7505, COX II nucleotides 7646 to 8329 and COX III nucleotides 9267 to 10052.

Diagnostic Detection of Alzheimer's Disease-Associated Mutations:

According to the present invention, base changes in the mitochondrial COX genes can be detected and used as a diagnostic for Alzheimer's disease. A variety of techniques are available for isolating DNA and RNA and for detecting mutations in the isolated mitochondrial COX genes.

A number of sample preparation methods are available for isolating DNA and RNA from patient blood samples. For example, the DNA from a blood sample can be obtained by cell lysis following alkali treatment. Often, there are multiple copies of RNA message per DNA. Accordingly, it is useful from the standpoint of detection sensitivity to have a sample preparation protocol which isolates both forms of nucleic acid. Total nucleic acid may be isolated by guanidium thiocyanate/phenol-chloroform extraction, or by proteinase K/phenol-chloroform treatment. Commercially available sample preparation methods such as those from Qiagen Inc. (Chatsworth, Calif.) can also be utilized.

As discussed more fully hereinbelow, hybridization with one or more of labelled probes containing the variant sequences enables detection of the AD mutations. Since each AD patient can be heteroplasmic (possessing both the AD mutation and the normal sequence) a quantitative or semi-quantitative measure (depending on the detection method) of such heteroplasmy can be obtained by comparing the amount of signal from the AD probe to the amount from the AD⁻ (normal) probe.

A variety of techniques, as discussed more fully hereinbelow, are available for detecting the specific mutations in the mitochondrial COX genes. The detection methods include, for example, cloning and sequencing, ligation of oligonucleotides, use of the polymerase chain reaction and variations thereof, use of single nucleotide primer-guided extension assays, hybridization techniques using target-specific oligonucleotides and sandwich hybridization methods.

Cloning and sequencing of the COX genes can serve to detect AD mutations in patient samples. Sequencing can be carried out with commercially available automated sequencers utilizing fluorescently labelled primers. An alternate sequencing strategy is the "sequencing by hybridization" method using high density oligonucleotide arrays on silicon chips (Fodor et al., *Nature* 364:555–556 (1993); Fodor et al., *Science* 251:767–773 (1991)). Fluorescently-labelled target nucleic acid generated, for example from PCR amplification of the target genes using fluorescently labelled primers, can be hybridized with a chip containing a set of short oligonucleotides which probe regions of complementarity with the target sequence. The resulting hybridization patterns can be used to reassemble the original target DNA sequence.

Mutational analysis can also be carried out by methods based on ligation of oligonucleotide sequences which anneal immediately adjacent to each other on a target DNA or RNA molecule (Wu and Wallace, *Genomics* 4:560–569 (1989); Landegrey et al., *Science* 241:1077–1080 (1988); Nickerson et al., *Proc. Natl. Acad. Sci.* 87:8923–8927 (1990); Barany, F., *Proc. Natl. Acad. Sci.* 88:189–193 (1991)). Ligase-mediated covalent attachment occurs only when the oligonucleotides are correctly base-paired. The Ligase Chain Reaction (LCR), which utilizes the thermostable Taq ligase for target amplification, is particularly useful for interrogating AD mutation loci. The elevated reaction temperatures permits the ligation reaction to be conducted with high stringency ( Barany, F., *PCR Methods and Applications* 1:5–16 (1991)).

Analysis of point mutations in DNA can also be carried out by using the polymerase chain reaction (PCR) and variations thereof. Mismatches can be detected by competitive oligonucleotide priming under hybridization conditions where binding of the perfectly matched primer is favored (Gibbs et al., *Nucl. Acids. Res.* 17:2437–2448 (1989)). In the amplification refractory mutation system technique (ARMS), primers can be designed to have perfect matches or mismatches with target sequences either internal or at the 3' residue (Newton et al., *Nucl. Acids. Res.* 17:2503–2516 (1989)). Under appropriate conditions, only the perfectly annealed oligonucleotide can function as a primer for the PCR reaction, thus providing a method of discrimination between normal and mutant (AD) sequences.

Genotyping analysis of the COX genes can also be carried out using single nucleotide primer-guided extension assays, where the specific incorporation of the correct base is provided by the high fidelity of the DNA polymerase (Syvanen et al., *Genomics* 8:684–692 (1990); Kuppuswamy et al., *Proc. Natl. Acad. Sci. U.S.A.* 88:1143–1147 (1991)).

Detection of single base mutations in target nucleic acids can be conveniently accomplished by differential hybridization techniques using target-specific oligonucleotides (Suggs et al., *Proc. Natl. Acad. Sci.* 78:6613–6617 (1981); Conner et al., *Proc. Natl. Acad. Sci.* 80:278–282 (1983); Saiki et al., *Proc. Natl. Acad. Sci.* 86:6230–6234 (1989)). Mutations can be diagnosed on the basis of the higher thermal stability of the perfectly matched probes as compared to the mismatched probes. The hybridization reactions can be carried out in a filter-based format, in which the target nucleic acids are immobilized on nitrocellulose or nylon membranes and probed with oligonucleotide probes. Any of the known hybridization formats may be used, including Southern blots, slot blots, "reverse" dot blots, solution hybridization, solid support based sandwich hybridization, bead-based, silicon chip-based and microtiter well-based hybridization formats.

An alternative strategy involves detection of the COX genes by sandwich hybridization methods. In this strategy, the mutant and wildtype (normal) target nucleic acids are separated from non-homologous DNA/RNA using a common capture oligonucleotide immobilized on a solid support and detected by specific oligonucleotide probes tagged with reporter labels. The capture oligonucleotides can be immobilized on microtitre plate wells or on beads (Gingeras et al., *J. Infect. Dis.* 164:1066–1074 (1991); Richman et al., *Proc. Natl. Acad. Sci.* 88:11241–11245 (1991)).

While radio-isotopic labeled detection oligonucleotide probes are highly sensitive, non-isotopic labels are preferred due to concerns about handling and disposal of radioactivity. A number of strategies are available for detecting target nucleic acids by non-isotopic means (Matthews et al., *Anal. Biochem.*, 169:1–25 (1988)). The non-isotopic detection method can be direct or indirect.

The indirect detection process is generally where the oligonucleotide probe is covalently labelled with a hapten or ligand such as digoxigenin (DIG) or biotin. Following the hybridization step, the target-probe duplex is detected by an antibody- or streptavidin-enzyme complex. Enzymes commonly used in DNA diagnostics are horseradish peroxidase and alkaline phosphatase. One particular indirect method, the Genius™ detection system (Boehringer Mannheim) is especially useful for mutational analysis of the mitochondrial COX genes. This indirect method uses digoxigenin as the tag for the oligonucleotide probe and is detected by an anti-digoxigenin-antibody-alkaline phosphatase conjugate.

Direct detection methods include the use of fluorophor-labeled oligonucleotides, lanthanide chelate-labeled oligonucleotides or oligonucleotide-enzyme conjugates. Examples of fluorophor labels are fluorescein, rhodamine and phthalocyanine dyes. Examples of lanthanide chelates include complexes of $Eu^{3+}$ and $Tb^{3+}$. Directly labeled oligonucleotide-enzyme conjugates are preferred for detecting point mutations when using target-specific oligonucleotides as they provide very high sensitivities of detection.

Oligonucleotide-enzyme conjugates can be prepared by a number of methods (Jablonski et al., *Nucl. Acids Res.*, 14:6115–6128 (1986); Li et al., *Nucl. Acids Res.* 15:5275–5287 (1987); Ghosh et al., *Bioconjugate Chem.* 1: 71–76 (1990)), and alkaline phosphatase is the enzyme of choice for obtaining high sensitivities of detection. The detection of target nucleic acids using these conjugates can be carried out by filter hybridization methods or by bead-based sandwich hybridization (Ishii et al., *Bioconjugate Chemistry* 4:34–41 (1993)).

Detection of the probe label can be accomplished by the following approaches. For radioisotopes, detection is by autoradiography, scintillation counting or phosphor imaging. For hapten or biotin labels, detection is with antibody or streptavidin bound to a reporter enzyme such as horseradish peroxidase or alkaline phosphatase, which is then detected by enzymatic means. For fluorophor or lanthanide-chelate labels, fluorescent signals can be measured with spectrofluorimeters with or without time-resolved mode or using automated microtitre plate readers. With enzyme labels, detection is by color or dye deposition (p-nitrophenyl phosphate or 5-bromo-4-chloro-3-indolyl phosphate/nitroblue tetrazolium for alkaline phosphatase and 3,3'-diaminobenzidine-NiCl$_2$ for horseradish peroxidase), fluorescence (e.g. 4-methyl umbelliferyl phosphate for alkaline phosphatase) or chemiluminescence (the alkaline phosphatase dioxetane substrates LumiPhos 530 from Lumigen Inc., Detroit, Mich. or AMPPD and CSPD from Tropix, Inc.). Chemiluminescent detection can be carried out with X-ray or polaroid film or by using single photon counting luminometers. This is the preferred detection format for alkaline phosphatase labelled probes.

The detection oligonucleotide probes can range in size between 10 and 100 bases, and are preferably between 15 and 30 bases in length. In order to obtain the required target discrimination using the detection oligonucleotide probes, the hybridization reactions are generally run between 20° and 60° C., and most preferably between 30° and 50° C. As known to those skilled in the art, optimal discrimination between perfect and mismatched duplexes can be obtained by manipulating the temperature and/or salt concentrations or inclusion of formamide in the stringency washes.

Therapeutic treatment of Alzheimer's Disease:

The destructive effect of the AD mutations in cytochrome oxidase genes can be reduced or eliminated using antisense oligonucleotide agents. Such antisense agents can target mitochondrial DNA, by triplex formation with double-stranded DNA, by duplex formation with single-stranded DNA during transcription, or both. Antisense agents can also target messenger RNA coding for the mutated cytochrome oxidase gene(s). Since the sequences of both the DNA and the mRNA are the same, it is not necessary to determine accurately the precise target to account for the desired effect.

To demonstrate the ability to affect expression of mitochondrial cytochrome oxidase genes, an oligonucleotide designed to hybridize near the 5'-end of the wild type COX I gene can be synthesized as in Example VI. When the antisense oligonucleotide is present in fibroblast culture, the cells are observed to die, as expected if the electron transport chain is interrupted. Control fibroblasts treated with complementary ('sense') oligonucleotide, or left untreated, showed no such effects.

Antisense oligonucleotide therapeutic agents demonstrate a high degree of pharmaceutical specificity. This allows the combination of two or more antisense therapeutics at the same time, without increased cytotoxic effects. Thus, when a patient is diagnosed as having two or more AD mutations in COX genes, the therapy can be tailored to treat the multiple mutations simultaneously. When combined with the present diagnostic test, this approach to "patient-specific therapy" results in treatment restricted to the specific mutations detected in a patient. This patient-specific therapy circumvents the need for 'broad spectrum' antisense treatment using all possible mutations. The end result is less costly treatment, with less chance for toxic side effects.

One method to inhibit the synthesis of proteins is through the use of antisense or triplex oligonucleotides, analogues or expression constructs. These methods entail introducing into the cell a nucleic acid sufficiently complementary in sequence so as to specifically hybridize to the target gene and can be extremely efficient since only a few copies per cell are required to achieve complete inhibition. Antisense methodology inhibits the normal processing, translation or half-life of the target message. Such methods are well known to one skilled in the art.

Antisense and triplex methods generally involve the treatment of cells or tissues with a relatively short oligonucleotide, although longer sequences can be used to achieve inhibition. The oligonucleotide can be either deoxyribo- or ribonucleic acid and must be of sufficient length to form a stable duplex or triplex with the target RNA or DNA at physiological temperatures and salt concentrations. It should also be of sufficient complementarity or sequence specificity to specifically hybridize to the target nucleic acid. Oligonucleotide lengths sufficient to achieve this specificity are generally about 10 to 60 nucleotides long, preferably about 10 to 20 nucleotides long. However, hybridization specificity is not only influenced by length and physiological conditions but may also be influenced by such factors as GC content and the primary sequence of the oligonucleotide. Such principles are well known in the art and can be routinely determined by one who is skilled in the art.

The composition of the antisense or triplex oligonucleotides can also influence the efficiency of inhibition. For example, it is preferable to use oligonucleotides that are resistant to degradation by the action of endogenous nucleases. Nuclease resistance will confer a longer in vivo half-life to the oligonucleotide, thus increasing its efficacy and reducing the required dose. Greater efficacy can also be obtained by modifying the oligonucleotide so that it is more permeable to cell membranes. Such modifications are well known in the art and include the alteration of the negatively charged phosphate backbone bases, or modification of the sequences at the $5^1$ or $3^1$ terminus with agents such as intercalators and crosslinking molecules. Specific examples of such modifications include oligonucleotide analogs that contain methylphosphonate (Miller, P.S., *Biotechnology*, 2:358–362 (1991)), phosphorothioate (Stein, *Science* 261:1004–1011 (1993)) and phosphorodithioate linkages (Brill, W. K-D., *J. Am. Chem. Soc.*, 111:2322 (1989)). Other types of linkages and modifications exist as well, such as a polyamide backbone in peptide nucleic acids (Nielson et al., *Science* 254:1497 (1991)), formacetal (Matteucci, M., *Tetrahedron Lett.* 31:2385–2388 (1990)) carbamate and morpholine linkages as well as others known to those skilled in the art. In addition to the specificity afforded by the antisense agents, the target RNA or genes can be irreversibly modified by incorporating reactive functional groups in these molecules which covalently link the target sequences e.g. by alkylation.

Recombinant methods known in the art can also be used to achieve the antisense or triplex inhibition of a target nucleic acid. For example, vectors containing antisense nucleic acids can be employed to express protein or antisense message to reduce the expression of the target nucleic acid and therefore its activity. Such vectors are known or can be constructed by those skilled in the art and should contain all expression elements necessary to achieve the desired transcription of the antisense or triplex sequences. Other beneficial characteristics can also be contained within the vectors such as mechanisms for recovery of the nucleic acids in a different form. Phagemids are a specific example of such beneficial vectors because they can be used either as plasmids or as bacteriophage vectors. Examples of other vectors include viruses, such as bacteriophages, baculoviruses and retroviruses, cosmids, plasmids, liposomes and other recombination vectors. The vectors can also contain elements for use in either procaryotic or eukaryotic host systems. One of ordinary skill in the art will know which host systems are compatible with a particular vector.

The vectors can be introduced into cells or tissues by any one of a variety of known methods within the art. Such methods are described for example in Sambrook et al., *Molecular Cloning: A Laboratory Manual*, Cold Spring Harbor Laboratory, New York (1992), which is hereby incorporated by references, and in Ausubel et al., *Current Protocols in Molecular Biology*, John Wiley and Sons, Baltimore, Md. (1989), which is also hereby incorporated by reference. The methods include, for example, stable or transient transfection, lipofection, electroporation and infection with recombinant viral vectors. Introduction of nucleic acids by infection offers several advantages over the other listed methods which includes their use in both in vitro and in vivo settings. Higher efficiency can also be obtained due to their infectious nature. Moreover, viruses are very specialized and typically infect and propagate in specific cell types. Thus, their natural specificity can be used to target the antisense vectors to specific cell types in vivo or within a tissue or mixed culture of cells. Viral vectors can also be modified with specific receptors or ligands to alter target specificity through receptor mediated events.

A specific example of a viral vector for introducing and expressing antisense nucleic acids is the adenovirus derived vector Adenop53TK. This vector expresses a herpes virus thymidine kinase (TK) gene for either positive or negative selection and an expression cassette for desired recombinant sequences such as antisense sequences. This vector can be used to infect cells including most cancers of epithelial origin, glial cells and other cell types. This vector as well as others that exhibit similar desired functions can be used to treat a mixed population of cells to selectively express the antisense sequence of interest. A mixed population of cells can include, for example, in vitro or ex vivo culture of cells, a tissue or a human subject.

Additional features can be added to the vector to ensure its safety and/or enhance its therapeutic efficacy. Such features include, for example, markers that can be used to negatively select against cells infected with the recombinant virus. An example of such a negative selection marker is the TK gene described above that confers sensitivity to the antibiotic gancyclovir. Negative selection is therefor a means by which infection can be controlled because it provides inducible suicide through the addition of antibiotics. Such protection ensures that if, for example, mutations arise that produce mutant forms of the viral vector or antisense sequence, cellular transformation will not occur. Moreover, features that limit expression to particular cell types can also be included. Such features include, for example, promoter and expression elements that are specific for the desired cell type.

The present invention is illustrated by, but not limited to, the following Examples.

EXAMPLES

Definitions of Abbreviations:

1 X SSC=150 mM sodium chloride, 15 mM sodium citrate, pH 6.5-8

SDS=sodium dodecyl sulfate

BSA=bovine serum albumin, fraction IV probe=a labelled nucleic acid, generally a single-stranded oligonucleotide, which is complementary to the DNA target immobilized on the membrane. The probe may be labelled with radioisotopes (such as $^{32}$p), haptens (such as digoxigenin), biotin, enzymes (such as alkaline phosphatase or horseradish peroxidase), fluorophores (such as fluorescein or Texas Red), or chemilumiphores (such as acridine).

PCR=polymerase chain reaction, as described by Erlich et al., *Nature* 331:461-462 (1988) hereby incorporated by reference.

EXAMPLE I

Isolation and cloning of cytochrome oxidase genes

DNA was obtained from AD patients and from non-Alzheimer's (normal) individuals. Normal individuals and AD patients were age-matched. AD patients were classified as probable AD by NINCDS criteria (McKann et al., *Neurology* 34:939-944 (1984)).

For blood samples, 6 ml samples were drawn, added to 18 ml of dextrane solution (3% dextrane, average MW=250,000 kiloDaltons (kDa), 0.9% sodium chloride, 1 mM ethylenedinitrilo tetraacetate), mixed and maintained at room temperature for 40 minutes without agitation to allow erythrocytes to sediment.

The plasma and leukocyte fraction was transferred to a centrifuge tube and leukocytes were collected by centrifugation at 14,000 x g for 5 minutes. The leukocyte pellet was resuspended in 3.8 ml of water and vortexed for 10 seconds to lyse remaining erythrocytes. 1.2 ml of 0.6 M sodium chloride was added and the sample was again centrifuged at 14,000 x g for 5 minutes to collect the leukocytes. The leukocyte pellet was resuspended in 0.4 ml of a solution containing 0.9% sodium chloride/1 mM ethylenedinitrilo tetraacetate and stored at −80° C.

Total cellular DNA was isolated from 0.2 ml of the frozen leukocyte sample. The frozen leukocytes were thawed, then collected by centrifugation at 14,000 x g in a microcentrifuge for 5 minutes. The cell pellet was washed three times with 0.8 ml of Dulbecco's Phosphate Buffered Saline (PBS; Gibco Laboratories, Life Technologies, Inc., Grand Island, N.Y.; catalog # 310- 4040AJ) and resuspended in 0.3 ml water. The leukocytes were lysed by adding 0.06 ml of 10% sodium dodecyl sulfate to the cell suspension, then incubating the samples for 10 minutes in a boiling water bath. After the samples had come to room temperature, cellular debris was pelleted by centrifugation at 14,000 x g for 5 minutes. The supernatant was transferred to a clean microcentrifuge tube and was extracted twice with 0.5 ml of phenol:chloroform (1:1) and twice with chloroform. DNA was precipitated by addition of 0.03 ml of 5M sodium chloride and 0.7 ml of 100% ethanol to the sample. Following incubation at −80° C., the precipitated DNA was collected by centrifugation at 14,000 x g for 15 minutes. The DNA pellet was washed with 0.8 ml of 80% ethanol, briefly dried, then resuspended in 0.2–0.4 ml of TE buffer (10mMTris-HCl, pH 7.5, 1 mM EDTA). The DNA concentration was determined by UV absorption at 260 nm.

For brain samples, total cellular DNA was isolated from 0.1–0.2 grams of frozen brain tissue. The frozen brain tissue was placed into a glass dounce homogenizer (Pyrex, VWR catalog #7726-S) containing 3 ml of lysis buffer (50mM Tris-HCl, pH 7.9, 100 mM EDTA, 0.1 M NaCl, 0.03 M dithiothreitol, 1% sodium dodecyl sulfate, 1 mg/ml proteinase K) and homogenized with a few strokes of the glass rod. The brain homogenate was transferred to an incubation tube and placed at 45°–50° C. for 30–60 minutes. After the addition of 5 ml of sterile water, the homogenate was extracted with phenol/chloroform two to three times, then twice with chloroform. DNA was precipitated by mixing the extracted sample with 1/20x volume of 5 M NaCl and 2.5x volumes of 200 proof ethanol and placed at −20° C. DNA was pelleted by centrifugation at 6,000xg for 15 minutes. The DNA pellet was washed with 10ml of 80% ethanol, briefly dried, and resuspended in 200–400 µl of TE buffer. The DNA concentration was determined by UV absorption at 260 nm.

The target cytochrome oxidase gene sequences were amplified by Polymerase Chain Reaction (PCR) (Erlich et al., Nature 331:461–462 (1988)). Primers were designed using the published Cambridge sequences for normal human COX genes. Primers were specific for COX gene sequences located approximately 100 nucleotides upstream and downstream of the mitochondrial COX genes encoding subunits I, II, and III. Primers had the following sequences: COX I-forward primer (5'-CAATATGAAAATCACCTCGGAGC-3') (SEQ. ID. NO. 4), COX I- reverse primer (5'-TTAGC-CTATAATTTAACTTTGAC- 3') (SEQ. ID. NO. 5), COX II-forward primer (5'-CAAGCCAACCCCATGGCCTCC-3') (SEQ. ID. NO. 6), COX II-reverse primer (5'-AGTATT-TAGTTGGGGCATTTCAC-3') (SEQ. ID. NO. 7), COX III-forward primer (5'-ACAATTCTAATTCTACTGAC-TATCC-3') (SEQ. ID. NO. 8), COX III-reverse primer, (5'-TTAGTAGTAAGGCTAGGAGGGTG- 3') (SEQ. ID. NO. 9).

Primers were chemically synthesized using a Cyclone Plus DNA Synthesizer (Millipore Corporation, Marlborough, Mass.) or a Gene assembler DNA Synthesizer (Pharmacia) utilizing beta-cyanoethylphosphoramidite chemistry. Newly synthesized primers were deprotected using ammonium hydroxide, lyophilized and purified by NAP-10 column chromatography (Pharmacia LKB Biotechnology Inc., Piscataway, N.J.; catalog # 17-0854-01). DNA concentration was determined by UV absorption at 260 nm.

Amplification was performed using 0.5–1.0 µg DNA in a reaction volume of 50–100 µl containing 10mM Tris-HCl, pH 8.3–9.5, 50 mM potassium chloride, 1–4 mM magnesium chloride, 200 µM each of dATP, dCTP, dGTP, and dTTP ("amplification cocktail"), 200 ng each of the appropriate COX forward and reverse primers and 5 units of AmpliTaq Polymerase (Perkin-Elmer Corporation; catalog # N801-0060).

Amplification using the GeneAmp PCR System 9600 (Perkin Elmer Corporation) was allowed to proceed for one cycle at 95° C. for 10 seconds, 25 cycles at 95° C. for 1 minute, 60° C. for 1 minute, 72° C. for 1 minute, one cycle at 72° C. for 4 minutes, after which the samples were cooled to 4° C. Five separate amplification reactions were performed for each patient and each cytochrome oxidase subunit. After the reactions were complete, the samples for each patient and subunit were combined and the amplified product was precipitated at −80° C. by the addition 1/10 volume of 5M sodium chloride and 2 volumes of 100% ethanol.

The PCR amplification product was pelleted by centrifugation, dried briefly, resuspended in 40 µl of TE buffer and purified by agarose gel electrophoresis (Sambrook et al., "Molecular Cloning: A Laboratory Manual," Cold Spring Harbor Laboratory, 1988). DNA was stained with ethidium bromide and visualized under long wavelength UV light. Bands of the expected lengths (approximately 1,700 bp for COX I, 900 bp for COX II and 1,000 bp for COX III) were excised from the gel. The gel containing the DNA was minced into small pieces and placed into a microcentrifuge tube. 0.3 ml of 1M sodium chloride was added to the gel fragments and the sample was frozen −80° C. then thawed and incubated at 50° C. for 15–20 minutes. Agarose was sedimented by centrifugation at 14,000 x g for 5 minutes, the supernatant containing the DNA was transferred to a new vial and the DNA fragments were collected by ethanol precipitation.

The amplified DNA fragments were cloned into the plasmid pCRII (Invitrogen Corp., San Diego, Calif.) using the TA-Cloning Kit (Invitrogen Corp., San Diego, Calif.; catalog #K2000-01). Ligations were performed in a reaction volume of 11 µl containing 1–5 µl of PCR amplification product, 2 µl of plasmid (50 ng), 1 µl of 10x ligation buffer and 1 µl of T4 DNA Ligase 4 units. Ligation reactions were incubated at 10°–12° C. for 15–16 hours.

Vector-ligated PCR fragments were transformed into competent E. coli cells strain XL1-Blue MRF' and Sure strain (Stratagene, San Diego, Calif.) using Epicurian Coli Competent Cells (catalog #'s 200230 and 200238, Stratagene, San Diego, Calif.). Transformed cells were spread onto LB-agar plates containing ampicillin (50 g/ml), kanamycin (50 g/ml), IPTG (isopropyl-B-D-thiogalactopyranoside, 20 mg/ml) and X-Gal (50 mg/ml). The blue/white color selection mechanism provided by the cloning vector in combination with the E. coli cells allowed for easy detection of recombinant clones, which were white.

Multiple white colonies were selected for each patient and COX subunit and screened by PCR for the presence of a correct insert using nested primers derived from the published Cambridge sequences. The primers were specific for sequences located approximately 40–60 nucleotides upstream and downstream of COX genes encoding subunits I, II and III. The sequences of the primers were as follows: COX I-forward primer (5'-AGGCCTAACCCCTGTC3') (SEQ. ID. NO. 10), COX I-reverse primer (5'-GGC-CATGGGGTTGGC-3') (SEQ. ID. NO. 11), COX II-forward primer (5'-AGGTATTAGAAAAACCA-3') (SEQ. ID. NO. 12), COX II-reverse primer (5'-ATCTTTAACTTAAAAGG) (SEQ. ID. NO. 13), COX III-forward primer (5'-GCCT-TAATCCAAGCC-3') (SEQ. ID. NO. 14), COX III-reverse primer (5'-GAATGTTGTCAAAACTAG-3') (SEQ. ID. NO. 15).

DNA samples from lysed cell supernatants were used as templates for PCR amplification. Individual colonies were selected and incubated overnight at 37° C. with shaking (225 rpm) in LB-broth containing ampicillin and kanamycin. 100–200 µl of each culture was centrifuged at 14,000 x g for 2 minutes. The cell pellet was resuspended in 5–10 µl of water, then lysed by incubation in a boiling water bath for 5 minutes. Cellular debris was removed by centrifugation at 14,000 x g for 2 minutes.

Amplification of the cloned DNA samples was performed in a reaction volume of 10 µl containing amplification cocktail, 40 ng each of the appropriate COX-S forward and reverse primers and 0.25 units of AmpliTaq Polymerase. Amplification was performed for one cycle at 95° C. for 10 seconds, 25 cycles at 95° C. for 1 minute, 44° C. for 1 minute, 72° C. for 1 minute, and cooled to 4° C. using the GeneAmp PCR System 9600. PCR products were analyzed by horizontal agarose gel electrophoresis.

EXAMPLE II

Sequencing of cytochrome oxidase (COX) genes

Plasmid DNA containing the COX gene inserts obtained as described in Example I was isolated using the Plasmid Quick® Plasmid Purification Kit (Stratagene, San Diego, Calif.) or the Plasmid Kit (Qiagen, Chatsworth, Calif., Catalog #12145. Plasmid DNA was purified from 50 ml bacterial cultures. For the Stratagene protocol "Procedure for Midi Columns," steps 10–12 of the kit protocol was replaced with a precipitation step using 2 volumes of 100% ethanol at −20° C., centrifugation at 6,000 x g for 15 minutes, a wash step using 80% ethanol and resuspension of the DNA sample in 100 µl TE buffer. DNA concentration was determined by horizontal agarose gel electrophorsis.

Sequencing reactions using double-stranded plasmid DNA were performed using the Sequenase Kit (United States Biochemical Corp., Cleveland, Ohio; catalog # 70770), the BaseStation T7 Kit (Millipore Corp.; catalog # MBBLSEQ01), the Vent Sequencing Kit (Millipore Corp; catalog #MBBLVEN01), the AmpliTaq Cycle Sequencing Kit (Perkin Elmer Corp.; catalog # N808-0110) and the Taq DNA Sequencing Kit (Boehringer Mannheim). The DNA sequences were detected by fluorescence using the BaseStation Automated DNA Sequencer (Millipore Corp.). For gene walking experiments, fluorescent oligonucleotide primers were synthesized on the Cyclone Plus DNA Synthesizer (Millipore Corp.) or the GeneAssembler DNA Synthesizer (Pharmacia LKB Biotechnology, Inc.) utilizing beta-cyanoethylphosphoramidite chemistry. The following primer sequences were prepared from the published Cambridge sequences of the COX genes for subunits I, II, and III, with fluorescein (F; FluoreDite fluorescein amidite, Millipore Corp.; or FluorePrime fluorescein amidite, Pharmacia LKB Biotechnology, Inc.) being introduced in the last step of automated DNA synthesis: COX I primer1 (5'-FAGGC-CTAACCCCTGTC-3') (SEQ. ID. NO. 16); COX I primer2 (5'-FGTCACAGCCCATG-3') (SEQ. ID. NO. 17); COX I primer3 (5'-FCCTGGAGCCTCCGTAG-3') (SEQ. ID. NO. 18); COX I primer4 (5'-FCTTCTTCGACCCCG-3') (SEQ. ID. NO. 19); COX I primer5 (5'-FCATATTTCACCTCCG-3') (SEQ. ID. NO. 20); COX I primer6 (5'-FCCTATCAAT-AGGAGC-3') (SEQ. ID. NO. 21); COX I primer7 (5'-FCATCCTATCATCTGTAGG-3') (SEQ. ID. NO. 22); COX II primer1 (5'-FAGGTATTAGAAAAACCA-3') (SEQ. ID. NO. 23); COX II primer2 (5'-FTAACTAATACTAACATCT-3') (SEQ. ID. NO. 24); COX II primer3 (5'-FTGCGACTC-CTTGAC-3') (SEQ. ID. NO. 25); COX III primer1 (5'-FGCCTTAATCCAAGCC-3') (SEQ. ID. NO. 26); COX III primer2 (5'- CAATGATGGCGCGATG-3') (SEQ. ID. NO. 27); COX III primer3 (5'-FCCGTATTACTCGCATCAGG-3') (SEQ. ID. NO. 28); COX III primer4 (5'-FCCGACG-GCATCTACGGC- 3' (SEQ. ID. NO. 29). Primers were deprotected and purified as described above. DNA concentration was determined by UV absorption at 260 nm.

Sequencing reaction were performed according to manufacturer's instructions except with the following modification: 1) the reactions were terminated and reduced in volume by heating the samples without capping to 94° C. for 5 minutes, after which 4 μl of stop dye (3 mg/ml dextran blue, 95%–99% formamide were added; as formulated by Millipore Corp.); 2) the temperature cycles performed for the AmpliTaq Cycle Sequencing Kit reactions and the Vent Sequencing kit reactions and the Taq Sequence Kit consisted of one cycle at 95° C. for 10 seconds, 30 cycles at 95° C. for 20 seconds, at 44° C. for 20 seconds and at 72° C. for 20 seconds followed by a reduction in volume by heating without capping to 94° C. for 5 minutes before adding 4 μl of stop dye.

Electrophoresis and gel analysis were performed using the BioImage and BaseStation Software provided by the manufacturer for the BaseStation Automated DNA Sequencer (Millipore Corp.). Sequencing gels were prepared according to the manufacturer's specifications. An average of ten different clones from each individual was sequenced. The resulting COX sequences were aligned and compared with published Cambridge sequences. Mutations in the derived sequence were noted and confirmed by resequencing the variant region.

Mutations in each COX gene for each individual were compiled. Comparisons of mutations between normal and AD patients were made and are summarized in Tables I and II.

EXAMPLE III

Detection of COX mutations by hybridization without prior amplification

This example illustrates taking test sample blood, blotting the DNA, and detecting by oligonucleotide hybridization in a dot blot format. This example uses two probes to determine the presence of the abnormal mutation at codon 22 of the COX II gene (see Table 1) in mitochondrial DNA of Alzheimer's patients. The Example utilizes a dot-blot format for hybridization, however, other known hybridization formats, such as Southern blots, slot blots, "reverse" dot blots, solution hybridization, solid support based sandwich hybridization, bead-based, silicon chip-based and microtiter well-based hybridization formats can also be used.

Sample Preparation Extracts and Blotting of DNA onto Membranes:

Whole blood is taken from the patient. The blood is mixed with an equal volume of 0.5–1N NaOH, and is incubated at ambient temperature for ten to twenty minutes to lyse cells, degrade proteins, and denature any DNA. The mixture is then blotted directly onto prewashed nylon membranes, in multiple aliquots. The membranes are rinsed in 10 x SSC (1.5M NaCl, 0.15M Sodium Citrate, pH 7.0) for five minutes to neutralize the membrane, then rinsed for five minutes in 1 X SSC. For storage, if any, membranes are air-dried and sealed. In preparation for hybridization, membranes are rinsed in 1 x SSC, 1% SDS.

Alternatively, 1–10 mls of whole blood is fractionated by standard methods, and the white cell layer ("buffy coat") is separated. The white cells are lysed, digested, and the DNA extracted by conventional methods (organic extraction, non-organic extraction, or solid phase). The DNA is quantitated by UV absorption or fluorescent dye techniques. Standardized amounts of DNA (0.1–5 μg) are denatured in base, and blotted onto membranes. The membranes are then rinsed.

Alternative methods of preparing cellular or mitochondrial DNA, such as isolation of mitochondria by mild cellular lysis and centrifugation, may also be used.

Hybridization and Detection:

For examples of synthesis, labelling, use, and detection of oligonucleotide probes, see "Oligonucleotides and Analogues: A Practical Approach", F. Eckstein, ed., Oxford University Press (1992); and "Synthetic Chemistry of Oligonucleotides and Analogs", S. Agrawal, ed., Humana Press (1993), which are incorporated herein by reference.

In this example the wild type COX II probe having the following sequence is used: ATC ATC CTA GTC CTC ATC GCC (SEQ ID NO 53)

For detection and quantitation of the abnormal mutation, membranes containing duplicate samples of DNA are hybridized in parallel; one membrane is hybridized with the normal probe, the other with the AD probe. Alternatively, the same membrane can be hybridized sequentially with both probes and the results compared.

For example, the membranes with immobilized DNA are hydrated briefly (10–60 minutes) in 1 x SSC, 1% SDS, then prehybridized and blocked in 5 x SSC, 1% SDS, 0.5% casein, for 30–60 minutes at hybridization temperature (35°–60° C., depending on which probe is used). Fresh hybridization solution containing probe (0.1–10 nM, ideally 2–3 nM) is added to the membrane, followed by hybridization at appropriate temperature for 15–60 minutes. The membrane is washed in 1 x SSC, 1% SDS, 1–3 times at 45°–60° C. for 5–10 minutes each (depending on probe used), then 1–2 times in 1 x SSC at ambient temperature. The hybridized probe is then detected by appropriate means.

The average proportion of AD COX gene to normal gene in the same patient can be determined by the ratio of the signal of the AD probe to the normal probe. This is a semiquantitative measure of % heteroplasmy in the AD patient and can be correlated to the severity of the disease.

EXAMPLE IV

Detection of COX mutations by hybridization (without prior amplification)

A. Slot-blot detection of RNA/DNA with $^{32}P$ probes

This example illustrates detection of COX mutations by slot-blot detection of DNA with $^{32}P$ probes. The reagents are prepared as follows: 4xBP: 2% (w/v)Bovine serum albumin (BSA), 2% (w/v) polyvinylpyrrolidone (PVP, Mol. Wt.: 40,000) is dissolved in sterile $H_2O$ and filtered through 0.22-µ cellulose acetate membranes (Corning) and stored at −20° C. in 50-ml conical tubes.

DNA is denatured by adding TE to the sample for a final volume of 90 µl. 10 µl of 2N NaOH is then added and the sample vortexed, incubated at 65° C. for 30 minutes, and then put on ice. The sample is neutralized with 100 ml of 2M ammonium acetate.

A wet piece of nitrocellulose or nylon is cut to fit the slot-blot apparatus according to the manufacturer's directions, and the denatured samples are loaded. The nucleic acids are fixed to the filter by baking at 80° C. under vacuum for 1 hr or exposing to UV light (254 nm). The filter is prehybridized for 10–30 minutes in ~5 mls of 1xBP, 5x SSPE, 1% SDS at the temperature to be used for the hybridization incubation. For 15–30-base probes, the range of hybridization temperatures is between 35°–60° C. For shorter probes or probes with low G-C content, a lower temperature must be used. At least $2 \times 10^6$ cpm of detection oligonucleotide per ml of hybridization solution is added. The filter is double sealed in Scotchpak™ heat sealable pouches (Kapak Corporation) and incubated for 90 min. The filter is washed 3 times at room temperature with 5-minute washes of 20X SSPE : 3M NaCl, 0.02M EDTA, 0.2 Sodium Phospate, pH 7.4, 1% SDS on a platform shaker. For higher stringency, the filter can be washed once at the hybridization temperature in 1X SSPE, 1% SDS for 1 minute. Visualization is by autoradiography on Kodak XAR film at −70° C. with an intensifying screen. To estimate the amount of target, compare the amount of target detected by visual comparison with hybridization standards of known concentration.

B. Detection of RNA/DNA by slot-blot analysis with alkaline phosphatase-oligonucleotide conjugate probes This example illustrates detection of COX mutations by slot-blot detection of DNA with alkaline phosphatase-oligonucleotide conjugate probes, using either a color reagent or a chemiluminescent reagent. The reagents are prepared as follows:

Color reagent: For the color reagent, the following are mixed together, fresh 0.16 mg/ml 5-bromo-4-chloro-3-indolyl phosphate (BCIP), 0.17 mg/ml nitroblue tetrazolium (NBT) in 100 mM NaCl, 100 mM Tris.HCl, 5 mM $MgCl_2$ and 0.1 mM $ZnCl_2$, pH 9.5.

Chemiluminescent reagent: For the chemiluminescent reagent, the following are mixed together, 250 µM 3-adamantyl 4-methoxy 4-(2-phospho)phenyl dioxetane (AMPPD), (Tropix Inc., Bedford, Mass.) in 100 mM diethanolamine-HCl, 1 mM $MgCl_2$ pH 9.5, or preformulated olioxetane substrate lumiphos™330 (Lumigen, Inc., Southfield, Mich.).

DNA target (0.01–50 fmol) is immobilized on a nylon membrane as described above. The filter is prehybridized in hybridization solution (5X SSC, 0.5% BSA, 0.1% SDS) for 10 minutes at the hybridization temperature (37°–60° C.) in a sealable bag using 50–100 µl of hybridization solution per cm of membrane. The solution is removed and briefly washed in warm hybridization buffer. The conjugate probe is then added to give a final concentration of 2–5 nM in fresh hybridization solution and final volume of 50–100 µl/cm² membrane. After incubating for 30 minutes at the hybridization temperature with agitation, the membrane is transferred to a wash tray containing 1.5 mol of preheated wash-1 solution (1X SSC, 1% SDS)/cm² of membrane and agitated at the wash temperature (usually optimum hybridization temperature minus 10° C.) for 10 minutes. Wash-1 solution is removed and wash-2 solution (1X SSC) added and then agitated at the wash temperature for 10 minutes. Wash-2 solution is removed and immediate detection is done by either color or chemiluminescense.

Detection by color is done by immersing the membrane fully in color reagent, and incubating at 20°–37° C. until color development is adequate. When color development is adequate, the development is quenched by washing in water.

Detection by chemiluminescence is done by immersing the membrane in luminescent reagent, using 25–50 µl solution/cc² of membrane. Kodak XAR-5 film (or equivalent; emission maximum is at 477 nm) is exposed in a light-tight cassette for 1–24 hours, and the film developed.

EXAMPLE V

Detection of COX mutations by amplification and hybridization

This example illustrates taking a test sample of blood, preparing DNA, amplifying a section of a specific COX gene by polymerase chain reaction (PCR), and detecting the mutation by oligonucleotide hybridization in a dot blot format.

Sample Preparation and Preparing of DNA:

Whole blood is taken from the patient. The blood is lysed, and the DNA prepared for PCR by using procedures described in Example 1.

Amplification of Target COX genes by Polymerase Chain Reaction, and Blotting onto Membranes:

The treated DNA from the test sample is amplified by using procedures described in Example 1. After amplification, the DNA is denatured, and blotted directly onto prewashed nylon membranes, in multiple aliquots. The membranes are rinsed in 10 x SSC for five minutes to neutralize the membrane, then rinsed for five minutes in 1 X SSC. For storage, if any, membranes are air-dried and sealed. In preparation for hybridization, membranes are rinsed in 1 x SSC, 1% SDS.

Hybridization and Detection:

Hybridization and detection of the amplified genes are accomplished as detailed in Example III.

Although the invention has been described with reference to the above-provided examples, it should be understood that various modifications can be made without departing from the spirit of the invention. Accordingly, the invention is limited only by the following claims.

---

We claim:

1. A method for aiding diagnosis of the presence of or screening for the risk of sporadic Alzheimer's disease in a subject, comprising the steps of:

a) obtaining a biological sample containing mitochondria from said subject; and b) determining the presence of at least one mutation in the sequence of a mitochondrial cytochrome oxidase gene obtained from said biological sample, wherein said at least one mutation correlates with the presence or risk of Alzheimer's disease.

2. A method according to claim 1 wherein the at least one mutation exists between codon 131 and codon 200 of the cytochrome oxidase I gene.

3. A method according to claim 1 wherein the at least one mutation is in the cytochrome oxidase I gene at a codon selected from the group consisting of codon 131, codon 155, codon 167, codon 178, codon 193, codon 194, and codon 415.

4. A method according to claim 1 wherein the at least one mutation exists between codon 20 and codon 150 of the cytochrome oxidase II gene.

5. A method according to claim 4 wherein the at least one mutation in the cytochrome oxidase II gene exists at a codon selected from the group consisting of codon 20, codon 22, codon 68, codon 71, codon 74, codon 95, codon 110, and codon 146.

6. A method according to claim 1 wherein the at least one mutation exists between codon 80 and codon 90 of the cytochrome oxidase III gene.

7. A method according to claim 6 wherein the at least one mutation in the cytochrome oxidase III gene exists at a codon selected from the group consisting of codon 82 and codon 89.

8. A method according to claim 1 wherein the presence of the at least one mutation in the sequence of a mitochondrial cytochrome oxidase gene is determined by hybridization of said gene with at least one oligonucleotide probe under conditions effective for detecting said mutation.

9. A method according to claim 1 wherein the presence of the at least one mutation in the sequence of a cytochrome oxidase gene is determined by a method based on ligation of oligonucleotide sequences which anneal immediately adjacent to each other on said cytochrome oxidase gene sequence, wherein ligase-mediated covalent attachment of the oligonucleotide sequences to one another occurs only when the oligonucleotides are correctly base-paired.

10. A method according to claim 9 wherein the method based on ligation of oligonucleotide sequences which anneal immediately adjacent to each other on said cytochrome oxidase gene sequence is the ligase chain reaction.

11. A method according to claim 1 wherein the presence of the at least one mutation in the sequence of a cytochrome oxidase gene is determined by using a polymerase chain reaction using at least one pair of primers.

12. A method according to claim 11 wherein in each pair of primers one primer is fully complementary to the gene sequence and the other primer contains a mismatch.

13. A method according to claim 12 wherein the mismatch is either internal or at the 3' end of said primer.

14. A method according to claim 1 wherein the presence of the at least one mutation in the sequence of a mitochondrial cytochrome oxidase gene is determined by single nucleotide primer-guided extension assays.

15. A method of determining the genetic mutations which are correlated with a predisposition to sporadic Alzheimer's disease, comprising the steps of:

a) determining the sequence of mitochondrial cytochrome oxidase genes from subjects known to have Alzheimer's disease;

b) comparing said sequence to that of known wildtype mitochondrial cytochrome oxidase genes; and c) identifying recurrent genetic mutations in the cytochrome oxidase germ in said subjects which correlate with said predisposition.

16. A method according to claim 1 wherein more than one mutation is detected.

* * * * *

UNITED STATES PATENT AND TRADEMARK OFFICE
CERTIFICATE OF CORRECTION

PATENT NO. : 5,565,323
DATED : Oct. 15, 1996
INVENTOR(S) : W. Davis Parker, et al It is certified that error appears in the above-indentified patent and that said Letters Patent is hereby corrected as shown below:

In the Abstract: Line 5: After "onset" insert --of--.

| Column | Line | |
|---|---|---|
| 6 | 20 | Change "is" to --are--. |
| 6 | 51 | Before "RNA" insert --an--. |
| 7 | 32 | Change "Taq" to --*Taq*--. |
| 7 | 35 | Change "permits" to --permit--. |
| 11 | 60 | Change "$^{32}$p)," to --$^{32}$P),--. |
| 14 | 20 | Change "(5'-AGGCCTAACCCCTGTC3')" to --(5'-AGGCCTAACCCCTGTC-3')--. |
| 14 | 61 | Change "electrophorsis" to --electrophoresis--. |

UNITED STATES PATENT AND TRADEMARK OFFICE
CERTIFICATE OF CORRECTION

PATENT NO. : 5,565,323
DATED : Oct. 15, 1996
INVENTOR(S) : W. Davis Parker, et al It is certified that error appears in the above-indentified patent and that said Letters Patent is hereby corrected as shown below:

| Column | Line | |
|---|---|---|
| 15 | 27 | Change "(5'-CAATGATGGCGCGATG-3')" to --(5'-FCAATGATGGCGCGATG-3')--. |
| 15 | 33 | Change "reaction" to --reactions--. |
| 56 | 7 | Change "germ" to --gene--. |

Signed and Sealed this

Twelfth Day of August, 1997

Attest:

BRUCE LEHMAN

Attesting Officer

Commissioner of Patents and Trademarks

SEQUENCE LISTING ( 1 ) GENERAL INFORMATION:

( i i i ) NUMBER OF SEQUENCES: 95

( 2 ) INFORMATION FOR SEQ ID NO:1:

( i ) SEQUENCE CHARACTERISTICS:

(A) LENGTH: 1613 base pairs
(B) TYPE: nucleic acid
(C) STRANDEDNESS: double
(D) TOPOLOGY: linear (xi) SEQUENCE DESCRIPTION: SEQ ID NO:1:

| | | | | | | |
|---|---|---|---|---|---|---|
| AGAGGCCTAA | CCCCTGTCTT | TAGATTTTAC | AGTCCAATGC | TTCACTCAGC | CATTTTACCT | 60 |
| CACCCCCACT | GATGTTCGCC | GACCGTTGAC | TATTCTCTAC | AAACCACAAA | GACATTGGAA | 120 |
| CACTATACCT | ATTATTCGGC | GCATGAGCTG | GAGTCCTAGG | CACAGCTCTA | AGCCTCCTTA | 180 |
| TTCGAGCCGA | GCTGGGCCAG | CCAGGCAACC | TTCTAGGTAA | CGACCACATC | TACAACGTTA | 240 |
| TCGTCACAGC | CCATGCATTT | GTAATAATCT | TCTTCATAGT | AATACCCATC | ATAATCGGAG | 300 |
| GCTTTGGCAA | CTGACTAGTT | CCCCTAATAA | TCGGTGCCCC | CGATATGGCG | TTTCCCCGCA | 360 |
| TAAACAACAT | AAGCTTCTGA | CTCTTACCTC | CCTCTCTCCT | ACTCCTGCTC | GCATCTGCTA | 420 |
| TAGTGGAGGC | CGGAGCAGGA | ACAGGTTGAA | CAGTCTACCC | TCCCTTAGCA | GGGAACTACT | 480 |
| CCCACCCTGG | AGCCTCCGTA | GACCTAACCA | TCTTCTCCTT | ACACCTAGCA | GGTGTCTCCT | 540 |
| CTATCTTAGG | GGCCATCAAT | TTCATCACAA | CAATTATCAA | TATAAACCCC | CTGCCATAA | 600 |
| CCCAATACCA | AACGCCCCTC | TTCGTCTGAT | CCGTCCTAAT | CACAGCAGTC | CTACTTCTCC | 660 |
| TATCTCTCCC | AGTCCTAGCT | GCTGGCATCA | CTATACTACT | AACAGACCGC | AACCTCAACA | 720 |
| CCACCTTCTT | CGACCCCGCC | GGAGGAGGAG | ACCCCATTCT | ATACCAACAC | CTATTCTGAT | 780 |
| TTTTCGGTCA | CCCTGAAGTT | TATATTCTTA | TCCTACCAGG | CTTCGGAATA | ATCTCCCATA | 840 |
| TTGTAACTTA | CTACTCCGGA | AAAAAGAAC | CATTTGGATA | CATAGGTATG | GTCTGAGCTA | 900 |
| TGATATCAAT | TGGATTCCTA | GGGTTTATCG | TGTGAGCACA | CCATATATTT | ACAGTAGGAA | 960 |
| TAGACGTAGA | CACACGAGCA | TATTTCACCT | CCGCTACCAT | AATCATCGCT | ATCCCCACCG | 1020 |
| GCGTCAAAGT | ATTTAGCTGA | CTCGCCACAC | TCCACGGAAG | CAATATGAAA | TGATCTGCTG | 1080 |
| CAGTGCTCTG | AGCCCTAGGA | TTCATCTTTC | TTTTCACCGT | AGGTGGCCTG | ACTGGCATTG | 1140 |
| TATTAGCAAA | CTCATCACTA | GACATCGTAC | TACACGACAC | GTACTACGTT | GTAGCCCACT | 1200 |
| TCCACTATGT | CCTATCAATA | GGAGCTGTAT | TTGCCATCAT | AGGAGGCTTC | ATTCACTGAT | 1260 |
| TTCCCCTATT | CTCAGGCTAC | ACCCTAGACC | AAACCTACGC | CAAAATCCAT | TTCACTATCA | 1320 |
| TATTCATCGG | CGTAAATCTA | ACTTTCTTCC | CACAACACTT | TCTCGGCCTA | TCCGGAATGC | 1380 |
| CCCGACGTTA | CTCGGACTAC | CCCGATGCAT | ACACCACATG | AAACATCCTA | TCATCTGTAG | 1440 |
| GCTCATTCAT | TTCTCTAACA | GCAGTAATAT | TAATAATTTT | CATGATTTGA | GAAGCTTCG | 1500 |
| CTTCGAAGCG | AAAAGTCCTA | ATAGTAGAAG | AACCCTCCAT | AAACCTGGAG | TGACTATATG | 1560 |
| GATGCCCCCC | ACCCTACCAC | ACATTCGAAG | AACCCGTATA | CATAAAATCT | AGA | 1613 |

(2) INFORMATION FOR SEQ ID NO:2:

(i) SEQUENCE CHARACTERISTICS:
(A) LENGTH: 754 base pairs
(B) TYPE: nucleic acid
(C) STRANDEDNESS: double
(D) TOPOLOGY: linear (xi) SEQUENCE DESCRIPTION: SEQ ID NO:2:

| | | | | | | |
|---|---|---|---|---|---|---|
| AGGTATTAGA | AAAACCATTT | CATAACTTTG | TCGTCAAAGT | TAAATTATAG | GCTAAATCCT | 60 |
| ATATATCTTA | ATGGCACATG | CAGCGCAAGT | AGGTCTACAA | GACGCTACTT | CCCCTATCAT | 120 |
| AGAAGAGCTT | ATCACCTTTC | ATGATCACGC | CCTCATAATC | ATTTTCCTTA | TCTGCTTCCT | 180 |
| AGTCCTGTAT | GCCCTTTTCC | TAACACTCAC | AACAAAACTA | ACTAATACTA | ACATCTCAGA | 240 |

| | | | | | |
|---|---|---|---|---|---|
| CGCTCAGGAA | ATAGAAACCG | TCTGAACTAT | CCTGCCCGCC | ATCATCCTAG | TCCTCATCGC | 300 |
| CCTCCCATCC | CTACGCATCC | TTTACATAAC | AGACGAGGTC | AACGATCCCT | CCCTTACCAT | 360 |
| CAAATCAATT | GGCCACCAAT | GGTACTGAAC | CTACGAGTAC | ACCGACTACG | GCGGACTAAT | 420 |
| CTTCAACTCC | TACATACTTC | CCCCATTATT | CCTAGAACCA | GGCGACCTGC | GACTCCTTGA | 480 |
| CGTTGACAAT | CGAGTAGTAC | TCCCGATTGA | AGCCCCCATT | CGTATAATAA | TTACATCACA | 540 |
| AGACGTCTTG | CACTCATGAG | CTGTCCCCAC | ATTAGGCTTA | AAAACAGATG | CAATTCCCGG | 600 |
| ACGTCTAAAC | CAAACCACTT | TCACCGCTAC | ACGACCGGGG | GTATACTACG | GTCAATGCTC | 660 |
| TGAAATCTGT | GGAGCAAACC | ACAGTTTCAT | GCCCATCGTC | CTAGAATTAA | TTCCCCTAAA | 720 |
| AATCTTTGAA | ATAGGGCCCG | TATTTACCCT | ATAG | | | 754 |

( 2 ) INFORMATION FOR SEQ ID NO:3:

( i ) SEQUENCE CHARACTERISTICS:
        ( A ) LENGTH: 856 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:3:

| | | | | | |
|---|---|---|---|---|---|
| TCGCTGTCGC | CTTAATCCAA | GCCTACGTTT | TCACACTTCT | AGTAAGCCTC | TACCTGCACG | 60 |
| ACAACACATA | ATGACCCACC | AATCACATGC | CTATCATATA | GTAAAACCCA | GCCCATGACC | 120 |
| CCTAACAGGG | GCCCTCTCAG | CCCTCCTAAT | GACCTCCGGC | CTAGCCATGT | GATTTCACTT | 180 |
| CCACTCCATA | ACGCTCCTCA | TACTAGGCCT | ACTAACCAAC | ACACTAACCA | TATACCAATG | 240 |
| ATGGCGCGAT | GTAACACGAG | AAAGCACATA | CCAAGGCCAC | CACACACCAC | CTGTCCAAAA | 300 |
| AGGCCTTCGA | TACGGGATAA | TCCTATTTAT | TACCTCAGAA | GTTTTTTTCT | TCGCAGGATT | 360 |
| TTTCTGAGCC | TTTTACCACT | CCAGCCTAGC | CCCTACCCCC | CAATTAGGAG | GGCACTGGCC | 420 |
| CCGAACAGGC | ATCACCCCGC | TAAATCCCCT | AGAAGTCCCA | CTCCTAAACA | CATCCGTATT | 480 |
| ACTCGCATCA | GGAGTATCAA | TCACCTGAGC | TCACCATAGT | CTAATAGAAA | ACAACCGAAA | 540 |
| CCAAATAATT | CAAGCACTGC | TTATTACAAT | TTACTGGGT | CTCTATTTTA | CCCTCCTACA | 600 |
| AGCCTCAGAG | TACTTCGAGT | CTCCCTTCAC | CATTTCCGAC | GGCATCTACG | GCTCAACATT | 660 |
| TTTTGTAGCC | ACAGGCTTCC | ACGGACTTCA | CGTCATTATT | GGCTCAACTT | TCCTCACTAT | 720 |
| CTGCTTCATC | CGCCAACTAA | TATTTCACTT | TACATCCAAA | CATCACTTTG | GCTTCGAAGC | 780 |
| CGCCGCCTGA | TACTGGCATT | TTGTAGATGT | GGTTGACTA | TTTCTGTATG | TCTCCATCTA | 840 |
| TTGATGAGGG | TCTTAC | | | | | 856 |

( 2 ) INFORMATION FOR SEQ ID NO:4:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:4:

| | | |
|---|---|---|
| CAATATGAAA | ATCACCTCGG | AGC | 23 |

( 2 ) INFORMATION FOR SEQ ID NO:5:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:5:

TTAGCCTATA ATTTAACTTT GAC  23

( 2 ) INFORMATION FOR SEQ ID NO:6:

( i ) SEQUENCE CHARACTERISTICS:
( A ) LENGTH: 21 base pairs
( B ) TYPE: nucleic acid
( C ) STRANDEDNESS: single
( D ) TOPOLOGY: linear ( x i ) SEQUENCE DESCRIPTION: SEQ ID NO:6:

CAAGCCAACC CCATGGCCTC C  21

( 2 ) INFORMATION FOR SEQ ID NO:7:

( i ) SEQUENCE CHARACTERISTICS:
( A ) LENGTH: 23 base pairs
( B ) TYPE: nucleic acid
( C ) STRANDEDNESS: single
( D ) TOPOLOGY: linear ( x i ) SEQUENCE DESCRIPTION: SEQ ID NO:7:

AGTATTTAGT TGGGGCATTT CAC  23

( 2 ) INFORMATION FOR SEQ ID NO:8:

( i ) SEQUENCE CHARACTERISTICS:
( A ) LENGTH: 25 base pairs
( B ) TYPE: nucleic acid
( C ) STRANDEDNESS: single
( D ) TOPOLOGY: linear ( x i ) SEQUENCE DESCRIPTION: SEQ ID NO:8:

ACAATTCTAA TTCTACTGAC TATCC  25

( 2 ) INFORMATION FOR SEQ ID NO:9:

( i ) SEQUENCE CHARACTERISTICS:
( A ) LENGTH: 23 base pairs
( B ) TYPE: nucleic acid
( C ) STRANDEDNESS: single
( D ) TOPOLOGY: linear ( x i ) SEQUENCE DESCRIPTION: SEQ ID NO:9:

TTAGTAGTAA GGCTAGGAGG GTG  23

( 2 ) INFORMATION FOR SEQ ID NO:10:

( i ) SEQUENCE CHARACTERISTICS:
( A ) LENGTH: 16 base pairs
( B ) TYPE: nucleic acid
( C ) STRANDEDNESS: single
( D ) TOPOLOGY: linear ( x i ) SEQUENCE DESCRIPTION: SEQ ID NO:10:

AGGCCTAACC CCTGTC  16

( 2 ) INFORMATION FOR SEQ ID NO:11:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO:11:

GGCCATGGGG TTGGC                                                            15

(2) INFORMATION FOR SEQ ID NO:12:

(i) SEQUENCE CHARACTERISTICS:
       (A) LENGTH: 17 base pairs
       (B) TYPE: nucleic acid
       (C) STRANDEDNESS: single
       (D) TOPOLOGY: linear (xi) SEQUENCE DESCRIPTION: SEQ ID NO:12:

AGGTATTAGA AAAACCA                                                          17

(2) INFORMATION FOR SEQ ID NO:13:

(i) SEQUENCE CHARACTERISTICS:
       (A) LENGTH: 17 base pairs
       (B) TYPE: nucleic acid
       (C) STRANDEDNESS: single
       (D) TOPOLOGY: linear (xi) SEQUENCE DESCRIPTION: SEQ ID NO:13:

ATCTTTAACT TAAAAGG                                                          17

(2) INFORMATION FOR SEQ ID NO:14:

(i) SEQUENCE CHARACTERISTICS:
       (A) LENGTH: 15 base pairs
       (B) TYPE: nucleic acid
       (C) STRANDEDNESS: single
       (D) TOPOLOGY: linear (xi) SEQUENCE DESCRIPTION: SEQ ID NO:14:

GCCTTAATCC AAGCC                                                            15

(2) INFORMATION FOR SEQ ID NO:15:

(i) SEQUENCE CHARACTERISTICS:
       (A) LENGTH: 18 base pairs
       (B) TYPE: nucleic acid
       (C) STRANDEDNESS: single
       (D) TOPOLOGY: linear (xi) SEQUENCE DESCRIPTION: SEQ ID NO:15:

GAATGTTGTC AAAACTAG                                                         18

(2) INFORMATION FOR SEQ ID NO:16:

(i) SEQUENCE CHARACTERISTICS:
       (A) LENGTH: 17 base pairs
       (B) TYPE: nucleic acid
       (C) STRANDEDNESS: single
       (D) TOPOLOGY: linear (ix) FEATURE:
       (A) NAME/KEY: misc_difference
       (B) LOCATION: replace(1, "")
       (D) OTHER INFORMATION: /note="N =fluorescein"

(xi) SEQUENCE DESCRIPTION: SEQ ID NO:16:

NAGGCCTAAC CCCTGTC                                                          17

(2) INFORMATION FOR SEQ ID NO:17:

(i) SEQUENCE CHARACTERISTICS:
       (A) LENGTH: 14 base pairs
       (B) TYPE: nucleic acid
       (C) STRANDEDNESS: single (D) TOPOLOGY: linear (ix) FEATURE:
 (A) NAME/KEY: misc_difference
 (B) LOCATION: replace(1, "")
 (D) OTHER INFORMATION: /note="N =fluorescein"

(xi) SEQUENCE DESCRIPTION: SEQ ID NO:17:

NGTCACAGCC CATG     14

(2) INFORMATION FOR SEQ ID NO:18:

(i) SEQUENCE CHARACTERISTICS:
  (A) LENGTH: 17 base pairs
  (B) TYPE: nucleic acid
  (C) STRANDEDNESS: single
  (D) TOPOLOGY: linear (ix) FEATURE:
  (A) NAME/KEY: misc_difference
  (B) LOCATION: replace(1, "")
  (D) OTHER INFORMATION: /note="N =fluorescein"

(xi) SEQUENCE DESCRIPTION: SEQ ID NO:18:

NCCTGGAGCC TCCGTAG     17

(2) INFORMATION FOR SEQ ID NO:19:

(i) SEQUENCE CHARACTERISTICS:
  (A) LENGTH: 15 base pairs
  (B) TYPE: nucleic acid
  (C) STRANDEDNESS: single
  (D) TOPOLOGY: linear (ix) FEATURE:
  (A) NAME/KEY: misc_difference
  (B) LOCATION: replace(1, "")
  (D) OTHER INFORMATION: /note="N =fluorescein"

(xi) SEQUENCE DESCRIPTION: SEQ ID NO:19:

NCTTCTTCGA CCCCG     15

(2) INFORMATION FOR SEQ ID NO:20:

(i) SEQUENCE CHARACTERISTICS:
  (A) LENGTH: 16 base pairs
  (B) TYPE: nucleic acid
  (C) STRANDEDNESS: single
  (D) TOPOLOGY: linear (ix) FEATURE:
  (A) NAME/KEY: misc_difference
  (B) LOCATION: replace(1, "")
  (D) OTHER INFORMATION: /note="N =fluorescein"

(xi) SEQUENCE DESCRIPTION: SEQ ID NO:20:

NCATATTTCA CCTCCG     16

(2) INFORMATION FOR SEQ ID NO:21:

(i) SEQUENCE CHARACTERISTICS:
  (A) LENGTH: 16 base pairs
  (B) TYPE: nucleic acid
  (C) STRANDEDNESS: single
  (D) TOPOLOGY: linear (ix) FEATURE:
  (A) NAME/KEY: misc_difference
  (B) LOCATION: replace(1, "")
  (D) OTHER INFORMATION: /note="N =fluorescein"

(xi) SEQUENCE DESCRIPTION: SEQ ID NO:21:

NCCTATCAAT AGGAGC                                                                                    16

( 2 ) INFORMATION FOR SEQ ID NO:22:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i x ) FEATURE:
        ( A ) NAME/KEY: misc_difference
        ( B ) LOCATION: replace(1, "")
        ( D ) OTHER INFORMATION: /note="N =fluorescein"

( x i ) SEQUENCE DESCRIPTION: SEQ ID NO:22:

NCATCCTATC ATCTGTAGG                                                                                 19

( 2 ) INFORMATION FOR SEQ ID NO:23:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i x ) FEATURE:
        ( A ) NAME/KEY: misc_difference
        ( B ) LOCATION: replace(1, "")
        ( D ) OTHER INFORMATION: /note="N =fluorescein"

( x i ) SEQUENCE DESCRIPTION: SEQ ID NO:23:

NAGGTATTAG AAAAACCA                                                                                  18

( 2 ) INFORMATION FOR SEQ ID NO:24:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i x ) FEATURE:
        ( A ) NAME/KEY: misc_difference
        ( B ) LOCATION: replace(1, "")
        ( D ) OTHER INFORMATION: /note="N =fluorescein"

( x i ) SEQUENCE DESCRIPTION: SEQ ID NO:24:

NTAACTAATA CTAACATCT                                                                                 19

( 2 ) INFORMATION FOR SEQ ID NO:25:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i x ) FEATURE:
        ( A ) NAME/KEY: misc_difference
        ( B ) LOCATION: replace(1, "")
        ( D ) OTHER INFORMATION: /note="N =fluorescein"

( x i ) SEQUENCE DESCRIPTION: SEQ ID NO:25:

NTGCGACTCC TTGAC                                                                                     15

( 2 ) INFORMATION FOR SEQ ID NO:26:

( i ) SEQUENCE CHARACTERISTICS:
        ( A ) LENGTH: 16 base pairs (B) TYPE: nucleic acid
        (C) STRANDEDNESS: single
        (D) TOPOLOGY: linear (ix) FEATURE:
        (A) NAME/KEY: misc_difference
        (B) LOCATION: replace(1, "")
        (D) OTHER INFORMATION: /note="N =fluorescein"

(xi) SEQUENCE DESCRIPTION: SEQ ID NO:26:

NGCCTTAATC CAAGCC                                                                          16

(2) INFORMATION FOR SEQ ID NO:27:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ix) FEATURE:
        (A) NAME/KEY: misc_difference
        (B) LOCATION: replace(1, "")
        (D) OTHER INFORMATION: /note="N =fluorescein"

(xi) SEQUENCE DESCRIPTION: SEQ ID NO:27:

NCAATGATGG CGCGATG                                                                         17

(2) INFORMATION FOR SEQ ID NO:28:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ix) FEATURE:
        (A) NAME/KEY: misc_difference
        (B) LOCATION: replace(1, "")
        (D) OTHER INFORMATION: /note="N =fluorescein"

(xi) SEQUENCE DESCRIPTION: SEQ ID NO:28:

NCCGTATTAC TCGCATCAGG                                                                      20

(2) INFORMATION FOR SEQ ID NO:29:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ix) FEATURE:
        (A) NAME/KEY: misc_difference
        (B) LOCATION: replace(1, "")
        (D) OTHER INFORMATION: /note="N =fluorescein"

(xi) SEQUENCE DESCRIPTION: SEQ ID NO:29:

NCCGACGGCA TCTACGGC                                                                        18

(2) INFORMATION FOR SEQ ID NO:30:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:30:

AGTCTACCCT CCCTTAGCAG G                                                                    21

( 2 ) INFORMATION FOR SEQ ID NO:31:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:31:

AGTCTACCCT ACCTTAGCAG GG 22

( 2 ) INFORMATION FOR SEQ ID NO:32:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:32:

ACCTAGCAGG TGTCTCCTCT ATC 23

( 2 ) INFORMATION FOR SEQ ID NO:33:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:33:

ACCTAGCAGG TATCTCCTCT ATCT 24

( 2 ) INFORMATION FOR SEQ ID NO:34:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:34:

CAATTTCATC ACAACAATTA TCAATAT 27

( 2 ) INFORMATION FOR SEQ ID NO:35:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:35:

CAATTTCATC ACAGCAATTA TCAATAT 27

( 2 ) INFORMATION FOR SEQ ID NO:36:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:36:

GCCATAACCC AATACCAAAC G 21

( 2 ) INFORMATION FOR SEQ ID NO:37:

( i ) SEQUENCE CHARACTERISTICS:
   ( A ) LENGTH: 21 base pairs
   ( B ) TYPE: nucleic acid
   ( C ) STRANDEDNESS: single
   ( D ) TOPOLOGY: linear ( x i ) SEQUENCE DESCRIPTION: SEQ ID NO:37:

GCCATAACCC TATACCAAAC G                                                21

( 2 ) INFORMATION FOR SEQ ID NO:38:

( i ) SEQUENCE CHARACTERISTICS:
      ( A ) LENGTH: 23 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:38:

AATCACAGCA GTCCTACTTC TCC                                              23

( 2 ) INFORMATION FOR SEQ ID NO:39:

( i ) SEQUENCE CHARACTERISTICS:
      ( A ) LENGTH: 23 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:39:

AATCACAGCA GCCCTACTTC TCC                                              23

( 2 ) INFORMATION FOR SEQ ID NO:40:

( i ) SEQUENCE CHARACTERISTICS:
      ( A ) LENGTH: 23 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:40:

AATCACAGCA ATCCTACTTC TCC                                              23

( 2 ) INFORMATION FOR SEQ ID NO:41:

( i ) SEQUENCE CHARACTERISTICS:
      ( A ) LENGTH: 25 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:41:

TCACAGCAGT CCTACTTCTC CTATC                                            25

( 2 ) INFORMATION FOR SEQ ID NO:42:

( i ) SEQUENCE CHARACTERISTICS:
      ( A ) LENGTH: 25 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:42:

TCACAGCAGT CTTACTTCTC CTATC                                            25

( 2 ) INFORMATION FOR SEQ ID NO:43:

( i ) SEQUENCE CHARACTERISTICS:

(A) LENGTH: 26 base pairs
(B) TYPE: nucleic acid
(C) STRANDEDNESS: single
(D) TOPOLOGY: linear (xi) SEQUENCE DESCRIPTION: SEQ ID NO:43:

CAAAATCCAT TTCACTATCA TATTCA 26

(2) INFORMATION FOR SEQ ID NO:44:

(i) SEQUENCE CHARACTERISTICS:
(A) LENGTH: 25 base pairs
(B) TYPE: nucleic acid
(C) STRANDEDNESS: single
(D) TOPOLOGY: linear (xi) SEQUENCE DESCRIPTION: SEQ ID NO:44:

AAAATCCATT TCGCTATCAT ATTCA 25

(2) INFORMATION FOR SEQ ID NO:45:

(i) SEQUENCE CHARACTERISTICS:
(A) LENGTH: 25 base pairs
(B) TYPE: nucleic acid
(C) STRANDEDNESS: single
(D) TOPOLOGY: linear (xi) SEQUENCE DESCRIPTION: SEQ ID NO:45:

TCATAGAAGA GCTTATCACC TTTCA 25

(2) INFORMATION FOR SEQ ID NO:46:

(i) SEQUENCE CHARACTERISTICS:
(A) LENGTH: 25 base pairs
(B) TYPE: nucleic acid
(C) STRANDEDNESS: single
(D) TOPOLOGY: linear (xi) SEQUENCE DESCRIPTION: SEQ ID NO:46:

TCATAGAAGA GCCTATCACC TTTCA 25

(2) INFORMATION FOR SEQ ID NO:47:

(i) SEQUENCE CHARACTERISTICS:
(A) LENGTH: 24 base pairs
(B) TYPE: nucleic acid
(C) STRANDEDNESS: single
(D) TOPOLOGY: linear (xi) SEQUENCE DESCRIPTION: SEQ ID NO:47:

AGAGCTTATC ACCTTTCATG ATCA 24

(2) INFORMATION FOR SEQ ID NO:48:

(i) SEQUENCE CHARACTERISTICS:
(A) LENGTH: 24 base pairs
(B) TYPE: nucleic acid
(C) STRANDEDNESS: single
(D) TOPOLOGY: linear (xi) SEQUENCE DESCRIPTION: SEQ ID NO:48:

AGAGCTTATC ATCTTTCATG ATCA 24

(2) INFORMATION FOR SEQ ID NO:49:

(i) SEQUENCE CHARACTERISTICS:
(A) LENGTH: 18 base pairs
(B) TYPE: nucleic acid ( C ) STRANDEDNESS: single
( D ) TOPOLOGY: linear ( x i ) SEQUENCE DESCRIPTION: SEQ ID NO:49:

TGAACTATCC TGCCCGCC                                                                                                18

( 2 ) INFORMATION FOR SEQ ID NO:50:

( i ) SEQUENCE CHARACTERISTICS:
( A ) LENGTH: 18 base pairs
( B ) TYPE: nucleic acid
( C ) STRANDEDNESS: single
( D ) TOPOLOGY: linear ( x i ) SEQUENCE DESCRIPTION: SEQ ID NO:50:

TGAACTATCT TGCCCGCC                                                                                                18

( 2 ) INFORMATION FOR SEQ ID NO:51:

( i ) SEQUENCE CHARACTERISTICS:
( A ) LENGTH: 18 base pairs
( B ) TYPE: nucleic acid
( C ) STRANDEDNESS: single
( D ) TOPOLOGY: linear ( x i ) SEQUENCE DESCRIPTION: SEQ ID NO:51:

TGCCCGCCAT CATCCTAG                                                                                                18

( 2 ) INFORMATION FOR SEQ ID NO:52:

( i ) SEQUENCE CHARACTERISTICS:
( A ) LENGTH: 18 base pairs
( B ) TYPE: nucleic acid
( C ) STRANDEDNESS: single
( D ) TOPOLOGY: linear ( x i ) SEQUENCE DESCRIPTION: SEQ ID NO:52:

TGCCCGCCAC CATCCTAG                                                                                                18

( 2 ) INFORMATION FOR SEQ ID NO:53:

( i ) SEQUENCE CHARACTERISTICS:
( A ) LENGTH: 21 base pairs
( B ) TYPE: nucleic acid
( C ) STRANDEDNESS: single
( D ) TOPOLOGY: linear ( x i ) SEQUENCE DESCRIPTION: SEQ ID NO:53:

ATCATCCTAG TCCTCATCGC C                                                                                            21

( 2 ) INFORMATION FOR SEQ ID NO:54:

( i ) SEQUENCE CHARACTERISTICS:
( A ) LENGTH: 21 base pairs
( B ) TYPE: nucleic acid
( C ) STRANDEDNESS: single
( D ) TOPOLOGY: linear ( x i ) SEQUENCE DESCRIPTION: SEQ ID NO:54:

ATCATCCTAA TCCTCATCGC C                                                                                            21

( 2 ) INFORMATION FOR SEQ ID NO:55:

( i ) SEQUENCE CHARACTERISTICS:
( A ) LENGTH: 21 base pairs
( B ) TYPE: nucleic acid
( C ) STRANDEDNESS: single
( D ) TOPOLOGY: linear ( x i ) SEQUENCE DESCRIPTION: SEQ ID NO:55:

GATCCCTCCC TTACCATCAA A                                                                 21

( 2 ) INFORMATION FOR SEQ ID NO:56:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:56:

GATCCCTCCT TTACCATCAA AT                                                                22

( 2 ) INFORMATION FOR SEQ ID NO:57:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:57:

GATCCCTCCC CTACCATCAA A                                                                 21

( 2 ) INFORMATION FOR SEQ ID NO:58:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:58:

AACCTACGAG TACACCGACT ACG                                                               23

( 2 ) INFORMATION FOR SEQ ID NO:59:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:59:

AACCTACGAG CACACCGACT AC                                                                22

( 2 ) INFORMATION FOR SEQ ID NO:60:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:60:

AACCTACGAG TGCACCGACT AC                                                                22

( 2 ) INFORMATION FOR SEQ ID NO:61:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:61:

AGTACTCCCG ATTGAAGCCC                                                                         20

( 2 ) INFORMATION FOR SEQ ID NO:62:

( i ) SEQUENCE CHARACTERISTICS:
          ( A ) LENGTH: 20 base pairs
          ( B ) TYPE: nucleic acid
          ( C ) STRANDEDNESS: single
          ( D ) TOPOLOGY: linear ( x i ) SEQUENCE DESCRIPTION: SEQ ID NO:62:

AGTACTCCCG GTTGAAGCCC                                                                         20

( 2 ) INFORMATION FOR SEQ ID NO:63:

( i ) SEQUENCE CHARACTERISTICS:
          ( A ) LENGTH: 21 base pairs
          ( B ) TYPE: nucleic acid
          ( C ) STRANDEDNESS: single
          ( D ) TOPOLOGY: linear ( x i ) SEQUENCE DESCRIPTION: SEQ ID NO:63:

CCTGCTAAGG GAGGGTAGAC T                                                                       21

( 2 ) INFORMATION FOR SEQ ID NO:64:

( i ) SEQUENCE CHARACTERISTICS:
          ( A ) LENGTH: 22 base pairs
          ( B ) TYPE: nucleic acid
          ( C ) STRANDEDNESS: single
          ( D ) TOPOLOGY: linear ( x i ) SEQUENCE DESCRIPTION: SEQ ID NO:64:

CCCTGCTAAG GTAGGGTAGA CT                                                                      22

( 2 ) INFORMATION FOR SEQ ID NO:65:

( i ) SEQUENCE CHARACTERISTICS:
          ( A ) LENGTH: 23 base pairs
          ( B ) TYPE: nucleic acid
          ( C ) STRANDEDNESS: single
          ( D ) TOPOLOGY: linear ( x i ) SEQUENCE DESCRIPTION: SEQ ID NO:65:

GATAGAGGAG ACACCTGCTA GGT                                                                     23

( 2 ) INFORMATION FOR SEQ ID NO:66:

( i ) SEQUENCE CHARACTERISTICS:
          ( A ) LENGTH: 24 base pairs
          ( B ) TYPE: nucleic acid
          ( C ) STRANDEDNESS: single
          ( D ) TOPOLOGY: linear ( x i ) SEQUENCE DESCRIPTION: SEQ ID NO:66:

AGATAGAGGA GATACCTGCT AGGT                                                                    24

( 2 ) INFORMATION FOR SEQ ID NO:67:

( i ) SEQUENCE CHARACTERISTICS:
          ( A ) LENGTH: 27 base pairs
          ( B ) TYPE: nucleic acid
          ( C ) STRANDEDNESS: single
          ( D ) TOPOLOGY: linear ( x i ) SEQUENCE DESCRIPTION: SEQ ID NO:67:

ATATTGATAA TTGTTGTGAT GAAATTG                                                                 27

( 2 ) INFORMATION FOR SEQ ID NO:68:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:68:

ATATTGATAA TTGCTGTGAT GAAATTG      27

( 2 ) INFORMATION FOR SEQ ID NO:69:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:69:

CGTTTGGTAT TGGGTTATGG C      21

( 2 ) INFORMATION FOR SEQ ID NO:70:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:70:

CGTTTGGTAT AGGGTTATGG C      21

( 2 ) INFORMATION FOR SEQ ID NO:71:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:71:

GGAGAAGTAG GACTGCTGTG ATT      23

( 2 ) INFORMATION FOR SEQ ID NO:72:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:72:

GGAGAAGTAG GGCTGCTGTG ATT      23

( 2 ) INFORMATION FOR SEQ ID NO:73:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:73:

GGAGAAGTAG GATTGCTGTG ATT      23

( 2 ) INFORMATION FOR SEQ ID NO:74:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:74:

GATAGGAGAA GTAGGACTGC TGTGA        25

( 2 ) INFORMATION FOR SEQ ID NO:75:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:75:

GATAGGAGAA GTAAGACTGC TGTGA        25

( 2 ) INFORMATION FOR SEQ ID NO:76:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:76:

TGAATATGAT AGTGAAATGG ATTTTG        26

( 2 ) INFORMATION FOR SEQ ID NO:77:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:77:

TGAATATGAT AGCGAAATGG ATTTT        25

( 2 ) INFORMATION FOR SEQ ID NO:78:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:78:

TGAAAGGTGA TAAGCTCTTC TATGA        25

( 2 ) INFORMATION FOR SEQ ID NO:79:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:79:

TGAAAGGTGA TAGGCTCTTC TATGA        25

( 2 ) INFORMATION FOR SEQ ID NO:80:

( i ) SEQUENCE CHARACTERISTICS:
   ( A ) LENGTH: 24 base pairs
   ( B ) TYPE: nucleic acid
   ( C ) STRANDEDNESS: single
   ( D ) TOPOLOGY: linear ( x i ) SEQUENCE DESCRIPTION: SEQ ID NO:80:

TGATCATGAA AGGTGATAAG CTCT 24

( 2 ) INFORMATION FOR SEQ ID NO:81:

( i ) SEQUENCE CHARACTERISTICS:
      ( A ) LENGTH: 24 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:81:

TGATCATGAA AGATGATAAG CTCT 24

( 2 ) INFORMATION FOR SEQ ID NO:82:

( i ) SEQUENCE CHARACTERISTICS:
      ( A ) LENGTH: 18 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:82:

GGCGGGCAGG ATAGTTCA 18

( 2 ) INFORMATION FOR SEQ ID NO:83:

( i ) SEQUENCE CHARACTERISTICS:
      ( A ) LENGTH: 18 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:83:

GGCGGGCAAG ATAGTTCA 18

( 2 ) INFORMATION FOR SEQ ID NO:84:

( i ) SEQUENCE CHARACTERISTICS:
      ( A ) LENGTH: 18 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:84:

CTAGGATGAT GGCGGGCA 18

( 2 ) INFORMATION FOR SEQ ID NO:85:

( i ) SEQUENCE CHARACTERISTICS:
      ( A ) LENGTH: 18 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:85:

CTAGGATGGT GGCGGGCA 18

( 2 ) INFORMATION FOR SEQ ID NO:86:

( i ) SEQUENCE CHARACTERISTICS:
      ( A ) LENGTH: 21 base pairs (B) TYPE: nucleic acid
(C) STRANDEDNESS: single
(D) TOPOLOGY: linear (xi) SEQUENCE DESCRIPTION: SEQ ID NO:86:

GGCGATGAGG ACTAGGATGA T                                                                    21

(2) INFORMATION FOR SEQ ID NO:87:

(i) SEQUENCE CHARACTERISTICS:
    (A) LENGTH: 21 base pairs
    (B) TYPE: nucleic acid
    (C) STRANDEDNESS: single
    (D) TOPOLOGY: linear (xi) SEQUENCE DESCRIPTION: SEQ ID NO:87:

GGCGATGAGG ATTAGGATGAT                                                                     21

(2) INFORMATION FOR SEQ ID NO:88:

(i) SEQUENCE CHARACTERISTICS:
    (A) LENGTH: 21 base pairs
    (B) TYPE: nucleic acid
    (C) STRANDEDNESS: single
    (D) TOPOLOGY: linear (xi) SEQUENCE DESCRIPTION: SEQ ID NO:88:

TTTGATGGTA AGGGAGGGAT C                                                                    21

(2) INFORMATION FOR SEQ ID NO:89:

(i) SEQUENCE CHARACTERISTICS:
    (A) LENGTH: 22 base pairs
    (B) TYPE: nucleic acid
    (C) STRANDEDNESS: single
    (D) TOPOLOGY: linear (xi) SEQUENCE DESCRIPTION: SEQ ID NO:89:

ATTTGATGGT AAAGGAGGGA TC                                                                   22

(2) INFORMATION FOR SEQ ID NO:90:

(i) SEQUENCE CHARACTERISTICS:
    (A) LENGTH: 21 base pairs
    (B) TYPE: nucleic acid
    (C) STRANDEDNESS: single
    (D) TOPOLOGY: linear (xi) SEQUENCE DESCRIPTION: SEQ ID NO:90:

TTTGATGGTA GGGGAGGGAT C                                                                    21

(2) INFORMATION FOR SEQ ID NO:91:

(i) SEQUENCE CHARACTERISTICS:
    (A) LENGTH: 23 base pairs
    (B) TYPE: nucleic acid
    (C) STRANDEDNESS: single
    (D) TOPOLOGY: linear (xi) SEQUENCE DESCRIPTION: SEQ ID NO:91:

CGTAGTCGGT GTACTCGTAG GTT                                                                  23

(2) INFORMATION FOR SEQ ID NO:92:

(i) SEQUENCE CHARACTERISTICS:
    (A) LENGTH: 22 base pairs
    (B) TYPE: nucleic acid
    (C) STRANDEDNESS: single ( D ) TOPOLOGY: linear ( x i ) SEQUENCE DESCRIPTION: SEQ ID NO:92:

GTAGTCGGTG TGCTCGTAGG TT 22

( 2 ) INFORMATION FOR SEQ ID NO:93:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:93:

GTAGTCGGTG CACTCGTAGG TT 22

( 2 ) INFORMATION FOR SEQ ID NO:94:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:94:

GGGCTTCAAT CGGGAGTACT 20

( 2 ) INFORMATION FOR SEQ ID NO:95:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:95:

GGGCTTCAAC CGGGAGTACT 20